US012788350B2

(12) United States Patent
Okumura et al.

(10) Patent No.: US 12,788,350 B2
(45) Date of Patent: Nov. 10, 2026

(54) X-RAY DIAGNOSIS APPARATUS AND X-RAY IMAGING CONTROL METHOD

(71) Applicant: Canon Kabushiki Kaisha, Tokyo (JP)

(72) Inventors: Yusuke Okumura, Nasushiobara (JP); Takahiro Inagaki, Nasushiobara (JP); Hideaki Tanaka, Otawara (JP); Naoki Yamada, Utsunomiya (JP); Hisanori Kato, Otawara (JP); Takanori Soutome, Nasushiobara (JP); Rui Moromizato, Nasushiobara (JP); Toshikatsu Oohashi, Otawara (JP)

(73) Assignee: Canon Kabushiki Kaisha, Tokyo (JP)

( * ) Notice: Subject to any disclaimer, the term of this patent is extended or adjusted under 35 U.S.C. 154(b) by 130 days.

(21) Appl. No.: 18/816,596

(22) Filed: Aug. 27, 2024

(65) Prior Publication Data

US 2025/0072857 A1 Mar. 6, 2025

(30) Foreign Application Priority Data

Aug. 28, 2023 (JP) ................................ 2023-137817
Aug. 9, 2024 (JP) ................................ 2024-134556

(51) Int. Cl.
*A61B 6/00* (2024.01)
*A61B 6/04* (2006.01)
(Continued)

(52) U.S. Cl.
CPC .............. *A61B 6/54* (2013.01); *A61B 6/0407* (2013.01); *A61B 6/06* (2013.01); *A61B 6/465* (2013.01); *A61B 6/469* (2013.01)

(58) Field of Classification Search
CPC ........... A61B 6/06; A61B 6/468; A61B 6/465; A61B 6/547; A61B 6/469; A61B 6/0407;
(Continued)

(56) References Cited

U.S. PATENT DOCUMENTS

2017/0055925 A1 3/2017 Lee et al.
2018/0368793 A1* 12/2018 Goto ...................... A61B 6/481
(Continued)

FOREIGN PATENT DOCUMENTS

EP 3 682 803 A1 7/2020
JP 2003-225235 A 8/2003

OTHER PUBLICATIONS

Extended European Search Report issued Dec. 6, 2024 in European Patent Application No. 24196584.7, 9 pages.

*Primary Examiner* — Irakli Kiknadze
(74) *Attorney, Agent, or Firm* — Oblon, McClelland, Maier & Neustadt, L.L.P.

(57) ABSTRACT

An X-ray diagnosis apparatus according to one embodiment includes an imaging system, a display, processing circuitry and system control circuitry. The imaging system includes an X-ray tube that generates an X-ray, an X-ray diaphragm that restricts an irradiation range of the X-ray, an X-ray detector that detects the X-ray, and a couch on which a subject is to be laid for irradiation with the X-ray. The display displays an X-ray image with numerical values indicating positions on the X-ray image generated by X-ray imaging of the subject by the imaging system. The processing circuitry recognizes a numerical value based on a collected user's utterance with respect to the numerical values. The system control circuitry performs control of the imaging system in accordance with a position indicated by the recognized numerical value among the numerical values.

20 Claims, 15 Drawing Sheets

(51) Int. Cl.
*A61B 6/06* (2006.01)
*A61B 6/46* (2024.01)

(58) Field of Classification Search
CPC ........... A61B 6/54; A61B 6/542; A61B 6/467; A61B 6/04; A61B 6/545; A61B 6/5241; A61B 6/587; A61B 6/4464; A61B 6/00; A61B 6/46; A61B 6/461; A61B 6/487; A61B 6/5294; A61B 6/5211; A61B 6/42; A61B 6/40; A61B 6/58; A61B 2560/0493; A61B 5/372; A61B 5/38; A61B 6/107; A61B 6/502; A61B 6/025; A61B 6/44; A61B 6/4035; A61B 6/504; A61B 6/4208; A61B 6/484; A61B 6/486; A61B 6/4452; A61B 6/481; A61B 6/0487; A61B 6/4441; A61B 6/464; A61B 6/4233; A61B 6/0457; A61B 6/12; A61B 6/10; A61B 6/4405; G06N 20/00; G10L 15/02; G10L 15/22; G10L 15/24; G10L 15/30; G10L 21/0232; G10L 21/12; G10L 25/18; H05G 1/06; H05G 1/30; G21K 1/046
USPC ................................................. 378/62, 98.12
See application file for complete search history.

(56) References Cited

U.S. PATENT DOCUMENTS

| | | | | |
|---|---|---|---|---|
| 2020/0330062 | A1 | 10/2020 | Lee et al. | |
| 2022/0296197 | A1 * | 9/2022 | Baumgart | A61B 6/469 |
| 2022/0346736 | A1 | 11/2022 | Lee et al. | |

* cited by examiner

X-RAY DIAGNOSIS APPARATUS AND X-RAY IMAGING CONTROL METHOD

CROSS-REFERENCE TO RELATED APPLICATIONS

This application is based upon and claims the benefit of priority from Japanese Patent Application No. 2023-137817, filed on Aug. 28, 2023; and Japanese Patent Application No. 2024-134556, filed on Aug. 9, 2024; the entire contents of which are incorporated herein by reference.

FIELD

Embodiments described herein relate generally to an X-ray diagnosis apparatus and an X-ray imaging control method.

BACKGROUND

With an X-ray diagnosis apparatus, an operator generally adjusts the diaphragm blades and/or the couch in position via a console while viewing a transparent image displayed on the monitor. Typically, a physician often treats a subject with both hands, therefore, the physician instructs a technician, i.e., the operator, to regulate the diaphragm aperture or operate the couch. In such a situation the physician may have difficulty in providing the operator with proper instructions as to the details of the operation.

DETAILED DESCRIPTION

Figure 1:
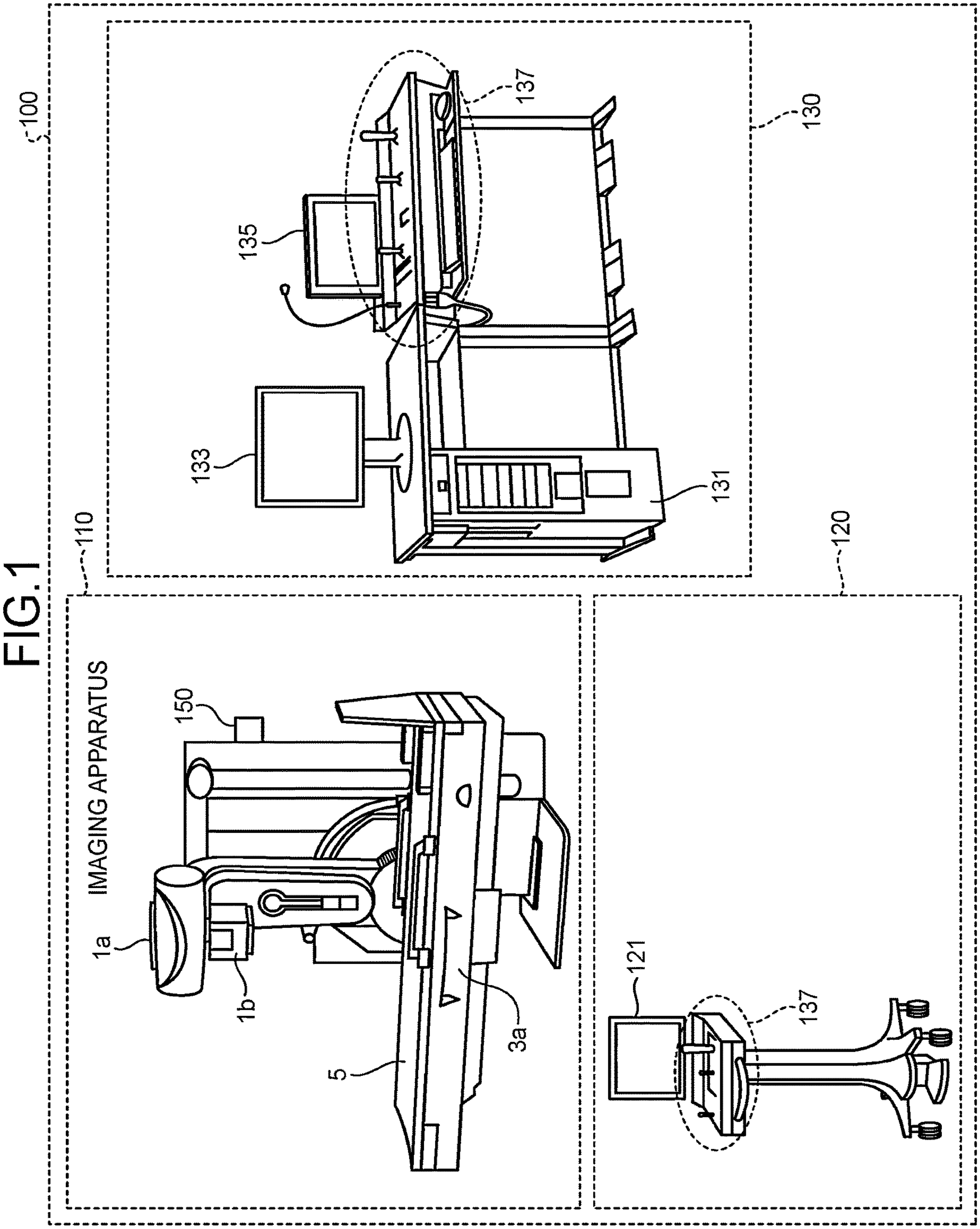
FIG. 1 illustrates one example of the exterior of an X-ray diagnosis apparatus according to an embodiment.

According to an embodiment, an X-ray diagnosis apparatus includes an imaging system, a display, processing circuitry and system control circuitry. The imaging system includes an X-ray tube that generates an X-ray, an X-ray diaphragm that restricts an irradiation range of the X-ray, an X-ray detector that detects the X-ray, and a couch on which a subject is to be laid for irradiation with the X-ray. The display displays an X-ray image with a plurality of numerical values indicating positions on the X-ray image generated by X-ray imaging of the subject by the imaging system. The processing circuitry is configured to recognize a numerical value based on a collected user's utterance with respect to the plurality of numerical values. The system control circuitry is configured to perform control of the imaging system in accordance with a position indicated by the recognized numerical value among the plurality of numerical values.

Hereinafter, exemplary embodiments of an X-ray diagnosis apparatus and an X-ray imaging control method will be described in detail with reference to the accompanying drawings. Throughout this disclosure, parts, portions, elements, or functions denoted by the same reference numerals are considered to perform same or similar operations, and an overlapping explanation thereof will be omitted when appropriate. In addition, the X-ray diagnosis apparatus according to some embodiments is defined as, but is not limited to, an X-ray diagnosis apparatus to be used in medical examination and treatment with respect to the digestive tract, urinary organs, orthopedics, and interventional radiology (IVR), as an example.

Embodiment

Referring to FIG. 1, an X-ray diagnosis apparatus 100 according to an embodiment is explained as an example. FIG. 1 shows an example of the exterior of the X-ray diagnosis apparatus 100 of an embodiment. As illustrated in FIG. 1, the X-ray diagnosis apparatus 100 of an embodiment includes a proximity operator station 120 equipped with an imaging apparatus (imaging system) 110 and a fluoroscopic monitor 121, a remote operator station 130 equipped with an image processing apparatus 131, a system monitor 133, and a fluoroscopic monitor 135, and a microphone 150, which are mutually connected in a wireless or wired manner. The imaging apparatus 110 includes an X-ray tube 1*a* that emits X-rays, an X-ray diaphragm 1*b* that restricts an X-ray irradiation range, an X-ray detector unit (or X-ray detector) 3 for X-ray detection, and a couch 5 on which a subject P is to be laid for X-ray irradiation. In the following, the microphone 150 is defined to be included in the imaging apparatus 110 for the sake of specificity.

For example, the operator such as a technician operates the remote operator station 130 from outside the examination room, e.g., an operation room, to cause the imaging apparatus 110 to raise or lower the couch 5 on which a patient (subject) is lying, and to vertically move the imaging system including the X-ray tube 1*a* and the X-ray diaphragm 1*b* and perform fluoroscopy or imaging of the patient at the same time. The operator then observes a fluoroscopic image displayed on the fluoroscopic monitor 135 of the remote operator station 130 and a captured image or a fluoroscopic image displayed on the system monitor 133. For another example, in the examination room the operator manipulates the proximity operator station 120 installed therein to perform a similar operation to the above operation, to observe various kinds of images displayed on the fluoroscopic monitor 121 of the proximity operator station 120 and on the monitor located in the examination room.

The remote operator station 130 and the proximity operator station 120 correspond to, for example, a console apparatus. As illustrated in FIG. 1, the console apparatus (remote operator station 130 and proximity operator station 120) includes an input device 137 with various kinds of buttons and levers for controlling the imaging apparatus 110, and output devices such as various kinds of monitors. The output devices correspond to, for example, displays such as the system monitor 133, the fluoroscopic monitor 135, and the fluoroscopic monitor 121. The input device 137 corresponds to any of various kinds of input interfaces. The input device 137 will be described below. For the sake of specificity, the console apparatus connected to the imaging apparatus 110 is defined as the remote operator station 130 herein.

Figure 2:
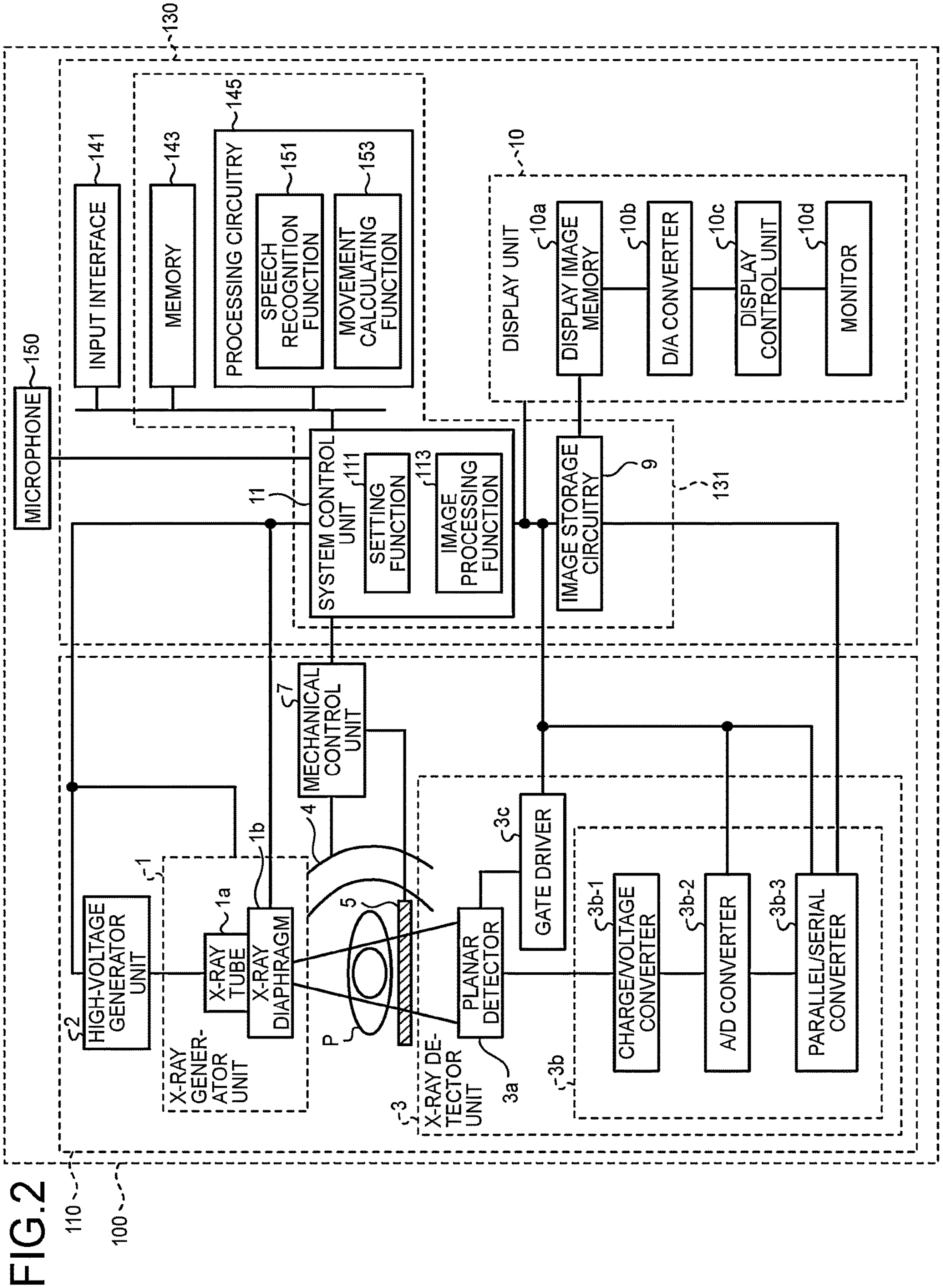
FIG. 2 is a block diagram illustrating one example of a configuration of an X-ray diagnosis apparatus according to an embodiment.

FIG. 2 illustrates one example of a configuration of the X-ray diagnosis apparatus 100 according to the present embodiment. The X-ray diagnosis apparatus 100 includes the imaging apparatus 110, a console apparatus 130, and the microphone 150. The imaging apparatus 110 includes an X-ray generator unit 1, a high-voltage generator unit 2, the X-ray detector unit 3, an arm 4, the couch 5, and a mechanical control unit 7. The imaging apparatus 110 and the console apparatus 130 may also be collectively referred to as an X-ray diagnosis system.

The X-ray generator unit 1 generates X-rays. The X-ray generator unit 1 includes, for example, the X-ray tube 1*a* and the X-ray diaphragm 1*b*. The X-ray generator unit 1 may be referred to as an X-ray generation apparatus. The X-ray tube 1*a* is, for example, a vacuum tube to be applied with a high voltage and supplied with a filament current from the X-ray high-voltage generator unit 2 to generate X-rays by emitting thermoelectrons from a negative pole (filament) to a positive pole (target). The X-rays are generated as a result of collision between the thermoelectrons and the target. Examples of the X-ray tube 1*a* include a rotating anode X-ray tube that generates X-rays by emitting thermoelectrons onto a rotating positive pole. The X-ray tube 1*a* can be any type in addition to the rotating anode type.

The X-ray diaphragm 1*b* shapes the X-ray irradiation field of the X-ray tube 1*a*. The X-ray diaphragm 1*b* is disposed in the front surface of the X-ray emission window of the X-ray tube 1*a*. The X-ray diaphragm 1*b* includes multiple diaphragm blades. For example, the X-ray diaphragm 1*b* may include two opposing diaphragm blades. Specifically, the X-ray diaphragm 1*b* may include, for example, four diaphragm blades made of metal plates such as lead. The four diaphragm blades are individually driven by a not-illustrated driver in accordance with a region of interest input by the operator via an input interface 141. The X-ray diaphragm 1*b* adjusts an X-ray shielded region to an optional size by sliding the diaphragm blades using the driver. The adjusted diaphragm blades of the X-ray diaphragm 1*b* can block X-rays outside the aperture area. In this manner the X-ray diaphragm 1*b* functions to restrict the X-rays from the X-ray tube 1*a* to irradiate the region of interest of the subject P.

The high-voltage generator unit 2 includes electric circuitry such as a transformer and a rectifier, and an X-ray controller. The high-voltage generator unit 2 functions to generate a high voltage to be applied to the X-ray tube 1*a* and a filament current to be supplied to the X-ray tube 1*a*. The high-voltage generator unit 2 may be referred to as a high-voltage generation apparatus. The X-ray controller controls the output voltage in accordance with the X-rays emitted from the X-ray tube 1*a*. The high-voltage generator unit 2 can be a transformer type or an inverter type. Further, the high-voltage generator unit 2 may be disposed in the arm 4.

The X-ray detector unit 3 detects X-rays emitted from the X-ray tube 1*a*. The X-ray detector unit 3 includes, for example, a planar detector 3*a* serving as an X-ray detector, an image data generator 3*b*, and a gate driver 3*c*. The planar detector 3*a* may be, for example, implemented by a flat panel detector (FPD). The FPD includes multiple semiconductor detector elements. There are two types of semiconductor detector elements, i.e., a direct conversion type that directly converts X-rays to electric signals and an indirect conversion type that uses a phosphor to convert X-rays to light and convert the light to electric signals. The FPD may include either of the types. The FPD outputs the electric signals to the image data generator 3*b*.

The image data generator 3*b* includes a charge/voltage converter 3*b*-1, an analog to digital (A/D) converter 3*b*-2, and a parallel/serial converter 3*b*-3. The charge/voltage converter 3*b*-1 converts the electric signals output from the planar detector 3*a* into voltage signals for output to the A/D converter 3*b*-2. Under the control of a system control unit 11, the A/D converter 3*b*-2 converts the voltage signals to digital data, i.e., X-ray image data, for output to the parallel/serial converter 3*b*-3. Under the control of the system control unit 11, the parallel/serial converter 3*b*-3 converts the X-ray image data as parallel data to serial data for output to image storage circuitry 9. The image data generator 3*b* may be referred to as an image data generation device.

The gate driver 3*c* drives the detector elements of the planar detector 3*a* under the control of the system control unit 11.

The arm 4 movably holds the X-ray tube 1*a* that generates X-rays and the planar detector 3*a* opposing the X-ray tube 1*a* to detect the X-rays. In other words, the X-ray tube 1*a* and the planar detector 3*a* are attached to an end of the arm 4, opposing each other. The arm 4 rotatably supports the X-ray diaphragm 1*b* and the planar detector 3*a* about the rotational axis, i.e., the line connecting between the center of the planar detector 3*a* and the focal point of the X-ray tube 1*a* generating X-rays. By operation of an arm moving mechanism, the arm 4 can rotate the X-ray diaphragm 1*b* and the planar detector 3*a* about the rotational axis. Alternatively, the arm 4 may hold the X-ray generator unit 1 and the X-ray detector unit 3 in a manner that the source-image distance (SID) is changeable, for example.

The couch 5 includes a couch top and a base. The subject P is to be laid on the couch top. The base supports the couch top movably in parallel along the long axis and the short axis of the couch top and in vertical direction. The base rotatably supports the couch top about rotational axes such as the long-axis and short-axis directions of the couch top and vertical direction.

A not-illustrated machinery unit (or mechanical device) includes an arm moving mechanism and a couch moving mechanism. The arm moving mechanism and the couch moving mechanism can be, for example, implemented by motors or actuators. The arm moving mechanism moves the arm 4 to a position as instructed by the operator or to a preset position under the control of the mechanical control unit 7. The couch moving mechanism moves the couch top of the couch 5 to a position as instructed by the operator or to a preset position under the control of the mechanical control unit 7.

The mechanical control unit 7 controls the machinery unit under the control of the system control unit 11. For example, the mechanical control unit 7 controls the operation of the arm moving mechanism and the operation of the couch moving mechanism in response to an operator's input via the input interface 141. Specifically, the mechanical control unit 7 retrieves and loads a mechanical control program from a storage onto the memory of its processor to control the operation of the arm moving mechanism and the operation of the couch moving mechanism according to the mechanical control program. The mechanical control unit 7 may be referred to as processing circuitry for controlling the machinery unit (mechanical control circuitry).

The microphone 150 collects a user's voice. For example, the user may be a physician that performs various kinds of procedures to the subject P. The microphone 150 includes electronic components that convert audio into electric signals. The microphone 150 outputs the collected voice to the remote operator station 130. As illustrated in FIG. 1 and FIG. 2, the microphone 150 is disposed in the imaging apparatus 110, however, the location of the microphone 150 is not limited thereto. Namely, the microphone 150 may be disposed on the ceiling and/or one of the walls of the examination room, or in the proximity operator station 120 as long as it can collect the user's voice.

The image processing apparatus 131 includes the image storage circuitry 9, the system control unit 11, a memory 143, and processing circuitry 145. The image storage circuitry 9 includes a hard disk drive (HDD) and semiconductor memory, for example. The image storage circuitry 9 stores therein X-ray image data output from the image data generator 3*b*.

The system control unit 11 performs control over the X-ray generator unit 1, the high-voltage generator unit 2, the gate driver 3*c*, the A/D converter 3*b*-2, the parallel/serial converter 3*b*-3, the mechanical control unit 7, the image storage circuitry 9, and a display unit 10 in accordance with inputs given from the operator via the input interface 141. Specifically, the system control unit 11 retrieves and loads a system control program onto its own memory to control the respective elements of the X-ray diagnosis apparatus 100 according to the control program. For example, the system control unit 11 subjects the X-ray image data stored in the image storage circuitry 9 to amplification and image computation to generate X-ray images for display.

The system control unit 11 further outputs an X-ray image from the image storage circuitry 9 to a display image memory 10*a* of the display unit 10, in response to an operator's instruction as to an image display, for instance. The system control unit 11 also outputs electric signals representing the voice output from the microphone 150 to the processing circuitry 145. The electric signals representing the voice may be directly output to the processing circuitry 145 without the system control unit 11. The system control unit 11 can be, for example, implemented by processing circuitry (also referred to as system control circuitry) that controls the respective elements of the X-ray diagnosis apparatus 100. The system control unit 11 may be simply referred to as a control unit.

Specifically, the system control unit 11 allows a setting function 111 to set a region of interest (ROI) in the X-ray image in accordance with an operator's instruction given via the input interface 141. The system control unit (system control circuitry) 11 implementing the setting function 111 corresponds to a setting unit. Further, the system control unit 11 allows the image processing function 113 to perform image processing to the overall X-ray image or the ROI, following an operator's instruction given via the input interface 141. The computer program for executing the image processing (image processing program) is stored in the memory 143, for example. The image processing function 113 retrieves and loads the image processing program from the memory 143 onto the memory in the system control unit 11 to perform the image processing by the image processing program. The system control unit (system control circuitry) 11 implementing the image processing function 113 corresponds to an image processing unit. The image processing can be any known image processing, therefore, a description thereof is omitted. Various types of image processing may be implemented by the processing circuitry 145 or separately provided image processing circuitry (not shown), in addition to the system control unit 11.

The display unit 10 includes the display image memory 10*a*, a digital to analog (D/A) converter 10*b*, a display control unit 10*c*, and a monitor 10*d*. The display image memory 10*a* stores the image data output from the image storage circuitry 9 for output to the D/A converter 10*b*. The D/A converter 10*b* converts the image data from the display image memory 10*a* to analog signals for output to the display control unit 10*c*. The display control unit 10*c* displays an X-ray image on the monitor 10*d* based on the image data output from the D/A converter 10*b*.

The display unit 10 may be implementable as a display and/or any of various kinds of monitors. Namely, the display unit 10 may correspond to, for example, the fluoroscopic monitor 121, the system monitor 133, or the fluoroscopic monitor 135 in FIG. 1. Examples of such a display include a liquid crystal display (LCD), a cathode ray tube (CRT) display, an organic electro luminescence display (OELD), a plasma display, and any other display when appropriate. The display may be a desk-top display or may include a tablet terminal wirelessly communicable with the system control unit 11 and the image storage circuitry 9. In addition, when the monitor 10*d* can display digital X-ray image data, the D/A converter 10*b* is omissible.

The input interface 141 receives various kinds of inputs from the operator to convert the inputs to electric signals and output them to the system control unit 11. The input interface 141 receives, from the operator, operational inputs for at least either of the arm 4 and the couch 5, X-ray generation conditions, image processing conditions, and operational inputs for the four diaphragm blades. Examples of the input interface 141 include a mouse, a keyboard, a trackball, a switch, a button, a joystick, a foot switch, a touch pad, and a touch panel display. The input interface 141 corresponds to the input device 137 of FIG. 1.

In the present embodiment, the input interface 141 is not limited to the one including physical operational components such as a mouse, a keyboard, a trackball, a switch, a button, a joystick, a touch pad, and a touch panel display.

Other examples of the input interface 141 include electric-signal processing circuitry that receives electric signals representing inputs from an exterior input device separated from the apparatus and outputs the electric signals to the system control unit 11. The input interface 141 may include a tablet terminal wirelessly communicable with the system control unit 11.

The memory 143 stores therein a computer program (speech recognition program) for implementing a speech recognition function 151. The memory 143 also stores a computer program (computation program) for implementing a movement calculating function 153. The speech recognition program refers to a computer program for recognizing a user's utterance or speech from electric signals representing a user's voice output from the microphone 150. As an example, the speech recognition program allows recognition of a numerical value or values included in the user's voice collected by the microphone 150. The speech recognition program can be any known speech recognition application, therefore, a description thereof is omitted.

The computation program refers to a computer program for calculating a moving amount of at least one of the devices included in the imaging system, based on the recognized numerical value and the current positions of the devices of the imaging system. The processing by the computation program relative to the movement calculating function 153 will be described later. The processing executed by the speech recognition program and the computation program involves displacement control of the various devices included in the imaging system and may be referred to as a voice moving-control process, which will be explained later.

The memory 143 stores therein position information as to various kinds of elements in the imaging apparatus 110 at the time of X-ray imaging of the subject P. Examples of the position information as to the various elements include the positions of the diaphragm blades in the X-ray diaphragm 1*b*, the position of the couch 5 relative to the X-ray tube 1*a*. Along with X-ray imaging, the position information is updated, for example, every time a fluoroscopic image is generated.

The memory 143 may be, for example, implemented by a storage device that stores various kinds of information, such as a HDD, a solid state drive (SSD), or an integrated circuit storage device. In addition to the HDD or SSD, the memory 143 can be a driver that reads and writes various kinds of information from and to portable storage media such as a compact disc (CD), a digital versatile disk (DVD), and a flash memory, and/or a semiconductor memory device as random access memory (RAM), for example.

The processing circuitry 145 calculates a moving amount for use in the voice moving-control process with respect to the imaging apparatus 110 by executing the speech recognition function 151 and the movement calculating function 153. The processing circuitry 145 uses the speech recognition function 151 to perform speech recognition of electric signals representing the voice from the microphone 150 upon receipt, to generate a result of the speech recognition (hereinafter, recognition result). The processing circuitry 145 implementing the speech recognition function 151 corresponds to a speech recognition unit. The processing circuitry 145 implementing the movement calculating function 153 corresponds to a movement calculator unit.

In the following, at least one of the diaphragm blades of the X-ray diaphragm 1*b* is defined to be controlled under the voice moving-control process for the sake of specificity. As an example, the user may pronounce "diaphragm, voice control". The expression "diaphragm, voice control" serves as activation words that initiate the voice moving-control process. In addition to "diaphragm, voice control", the activation words can be any other spoken words such as "voice control, diaphragm" as long as the words represent the intention to control the diaphragm by voice. Examples of other spoken words may include terms associated with words used in a physician's diaphragm control instruction to a technician. The microphone 150 collects the voice to generate and output electric signals corresponding to the voice to the remote operator station 130. The speech recognition function 151 recognizes that the diaphragm is to undergo the voice moving-control process from the user's speech. The speech recognition function 151 outputs to the system control unit 11 a recognition result indicating the diaphragm as an object to be controlled (hereinafter, referred to as a diaphragm control instruction).

The object to be controlled under the voice moving-control process is not limited to the diaphragm blades. For example, for the couch 5 to be controlled under the voice moving-control process, the activation words may be "couch, voice control", for instance. An example that an object other than the diaphragm blades is subject to the voice moving-control process will be explained later in a modification.

Triggered by receipt of the diaphragm control instruction, the system control unit 11 displays on the display unit 10 (display) an X-ray image of the subject P resulting from X-ray imaging by the imaging apparatus 110 and multiple numerical values indicating positions on the X-ray image. In other words, in response to receipt of the diaphragm control instruction, the display unit 10 displays the X-ray image with the numerical values indicating the positions. In addition, the display unit 10 may further display multiple scales corresponding to the multiple numerical values.

After uttering "diaphragm, voice control", the user utters the locations of the diaphragm blades to be moved and numerical values indicating the coordinates of the destinations of the diaphragm blades. The locations of the diaphragm blades correspond to top, bottom, right, and left in the X-ray image displayed on the display unit 10. The numerical values indicating the coordinates of the destinations of the diaphragm blades correspond to numerical values (coordinate values) displayed on the display unit 10. For example, the coordinates of the destinations represent positions in the coordinate system set to the X-ray image displayed on the display unit 10. The origin of the coordinate system is, for example, set to the top left end of the X-ray image displayed on the display unit 10. The origin of the coordinate system is optionally settable. The coordinate system is stored in the memory 143 in association with the position information as to the various kinds of elements of the imaging apparatus 110. Thus, the memory 143 stores therein a table representing the correspondence between the position information and the coordinate system (hereinafter, a position-coordinate table), for example.

To move the left-side diaphragm blade relative to the X-ray image to the position of a numerical value of 15, for example, the words "left diaphragm, 15" may be uttered to specify the location of the diaphragm blade to be moved and the numerical value indicating the coordinate of the destination of the diaphragm blade. This utterance denotes that the left-side diaphragm blade relative to the X-ray image is moved to the coordinate "15" displayed with the X-ray image. In addition to the words "left diaphragm, 15", the words to express the location of the diaphragm blade to be moved and the numerical value indicating the coordinate of the destination of the diaphragm blade may be any other words, such as "15, left diaphragm".

The microphone 150 collects the user's voice uttering the location of the diaphragm blade to be moved and the numerical value indicating the coordinate of the destination of the diaphragm blade (hereinafter, moving instruction words), to output electric signals representing the moving instruction words to the remote operator station 130. The speech recognition function 151 recognizes, for example, one of the two opposing diaphragm blades from the user's speech, i.e., the moving instruction words. Specifically, the speech recognition function 151 recognizes, from the user's moving instruction words, the location of the diaphragm blade to be controlled by the voice moving-control process and the numerical value indicating the coordinate of the destination of the diaphragm blade. The speech recognition function 151 then outputs, to the movement calculating function 153, information to identify the diaphragm blade to be moved and the recognition result indicating the coordinate of the destination (hereinafter, diaphragm moving instruction).

The processing circuitry 145 uses the movement calculating function 153 to calculate a moving amount of the object concerned according to the diaphragm moving instruction. For example, the movement calculating function 153 obtains current position information of the diaphragm blade to be moved and the position-coordinate table from the memory 143 to calculate a moving amount of the diaphragm blade based on the current position information, the position-coordinate table, and the coordinate of the destination. The movement calculating function 153 outputs the resultant moving amount to the system control unit 11. The system control unit 11 then moves the object concerned (e.g., diaphragm blade) by the moving amount.

Namely, the system control unit 11 performs control of the imaging apparatus 110 with reference to the position (coordinate of the destination of the object) indicated by the recognized numerical value among the numerical values displayed together with the X-ray image on the display unit 10. For example, the system control unit 11 controls the X-ray diaphragm 1*b* to move at least one of the diaphragm blades to the position corresponding to the recognized numerical value. Specifically, the system control unit 11 performs control over the X-ray diaphragm 1*b* to move one of the two opposing diaphragm blades to the position corresponding to the recognized numerical value.

The processing circuitry 145 and the processing circuitry implementing the mechanical control unit 7 and the system control unit 11 each include hardware resources, i.e., a processor such as a CPU, a micro processing unit (MPU), a graphical processing unit (GPU), and memory such as read-only memory (ROM) and random access memory (RAM), for example. The processing circuitry may be implemented by a processor such as an application specific integrated circuit (ASIC), a field programmable gate array (FPGA), another complex programmable logic device (CPLD), or a simple programmable logic device (SPLD).

The respective functions to be executed by the processor are stored in a computer-executable program format in a not-illustrated memory. The processor can implement the functions corresponding to the computer programs by retrieving and executing the computer programs from the memory. In other words, having retrieved the computer programs, the respective circuits include the functions corresponding to the computer programs.

The overall configuration of the X-ray diagnosis apparatus 100 of one embodiment has been described above. According to one embodiment, the X-ray diagnosis apparatus 100 configured above displays an X-ray image with numerical values of a coordinate system and scales in response to a user's utterance of the activation words, and executes the voice moving-control process to move the imaging system in response to a user's utterance of the diaphragm moving instruction. The following will describe steps of the voice moving-control process as an example, referring to FIG. 3 to FIG. 7.

Figure 3:
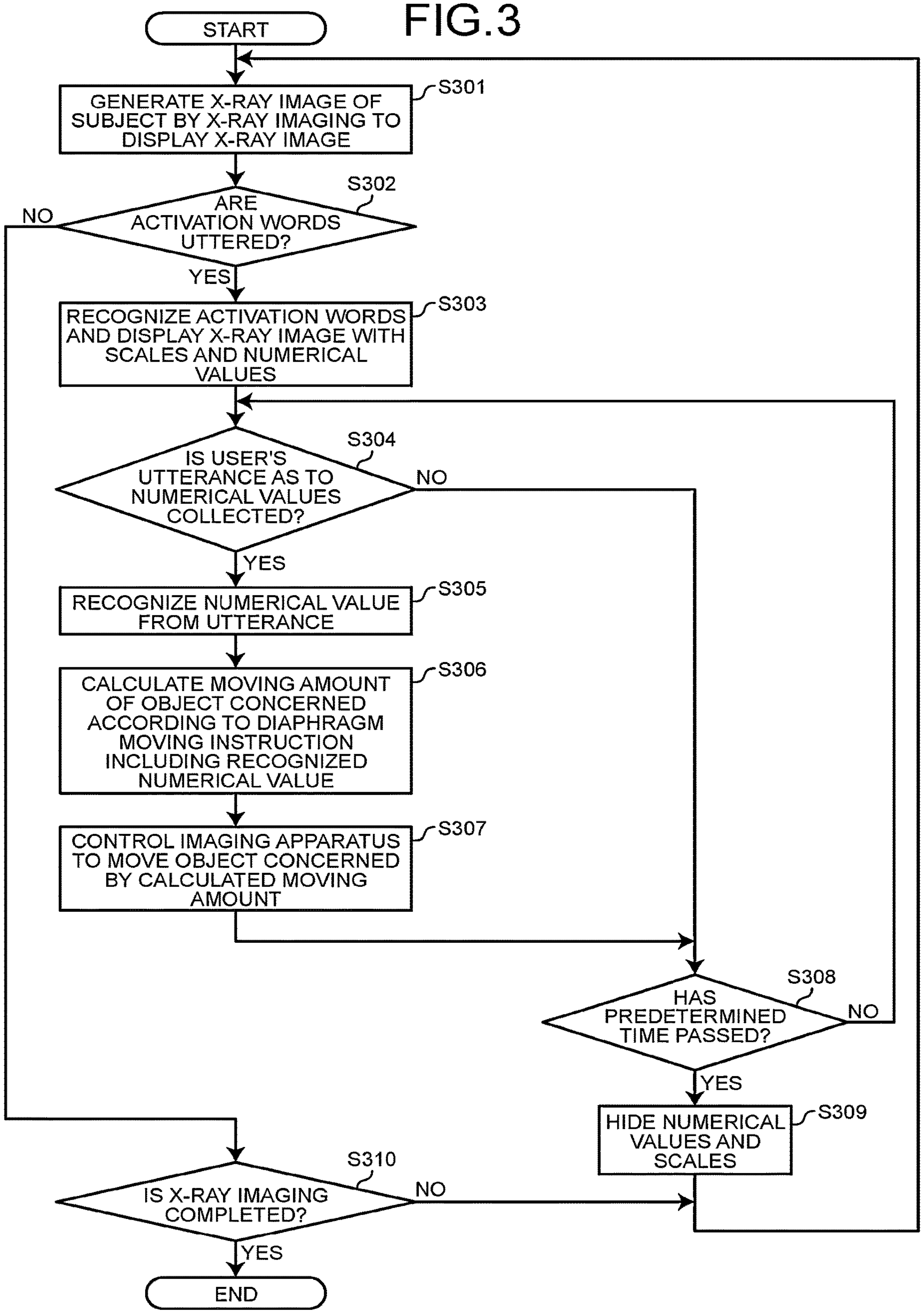
FIG. 3 is a flowchart illustrating a voice moving-control procedure according to an embodiment by way of example.
Figure 4:
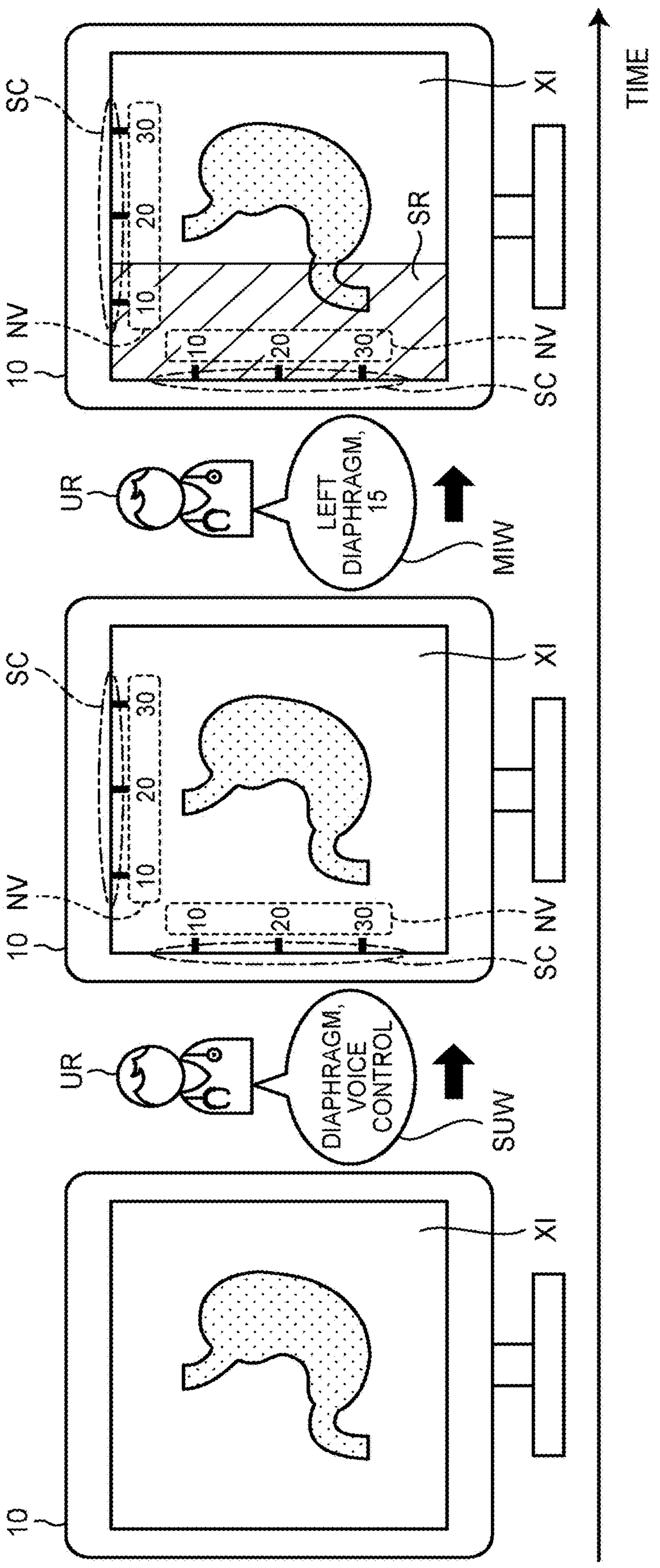
FIG. 4 illustrates an outline of the voice moving-control process procedure according to an embodiment by way of example.

FIG. 3 is a flowchart illustrating exemplary steps of the voice moving-control process. In the present embodiment the diaphragm blade is defined as an exemplary object to be controlled by the voice moving-control process, as described above. FIG. 4 depicts an example of the outline of the voice moving-control process.

Voice Moving-Control Process

Step S301

The imaging apparatus 110 generates an X-ray image XI of the subject P by irradiating the subject P with X-rays. Position information on the diaphragm blade at the time of the X-ray irradiation is defined as current position information and stored in the memory 143. The display unit 10 displays the X-ray image XI.

Step S302

A user UR utters activation words SUW "diaphragm, voice control" (YES at step S302). The microphone 150 then collects the utterance of the activation words SUW, and converts the utterance to electric signals for output to the remote operator station 130. The process then proceeds to step S303. When the user UR utters no activation words SUW (No at step S302), the process proceeds to step S310.

Step S303

The processing circuitry 145 uses the speech recognition function 151 to recognize the activation words SUW. Thereby, the speech recognition function 151 identifies an object to be controlled by the voice moving-control process. In response to the recognition of the activation words SUW, the system control unit 11 displays multiple numerical values NV on the X-ray image XI displayed on the display unit 10. The numerical values NV indicate positions on the X-ray image XI. Thus, after the utterance of the activation words SUW, the display unit 10 displays the X-ray image XI of the subject P generated by X-ray imaging using the imaging apparatus 110 and the numerical values NV representing the positions (coordinates indicating movable positions of diaphragm blades) on the X-ray image XI. The display unit 10 may additionally display multiple scales SC corresponding to the numerical values NV. In the example of FIG. 4, the numerical values NV and the scales SC are displayed along the longitudinal and lateral sides of the X-ray image XI, in response to the utterance of the activation words SUW.

Figure 5:
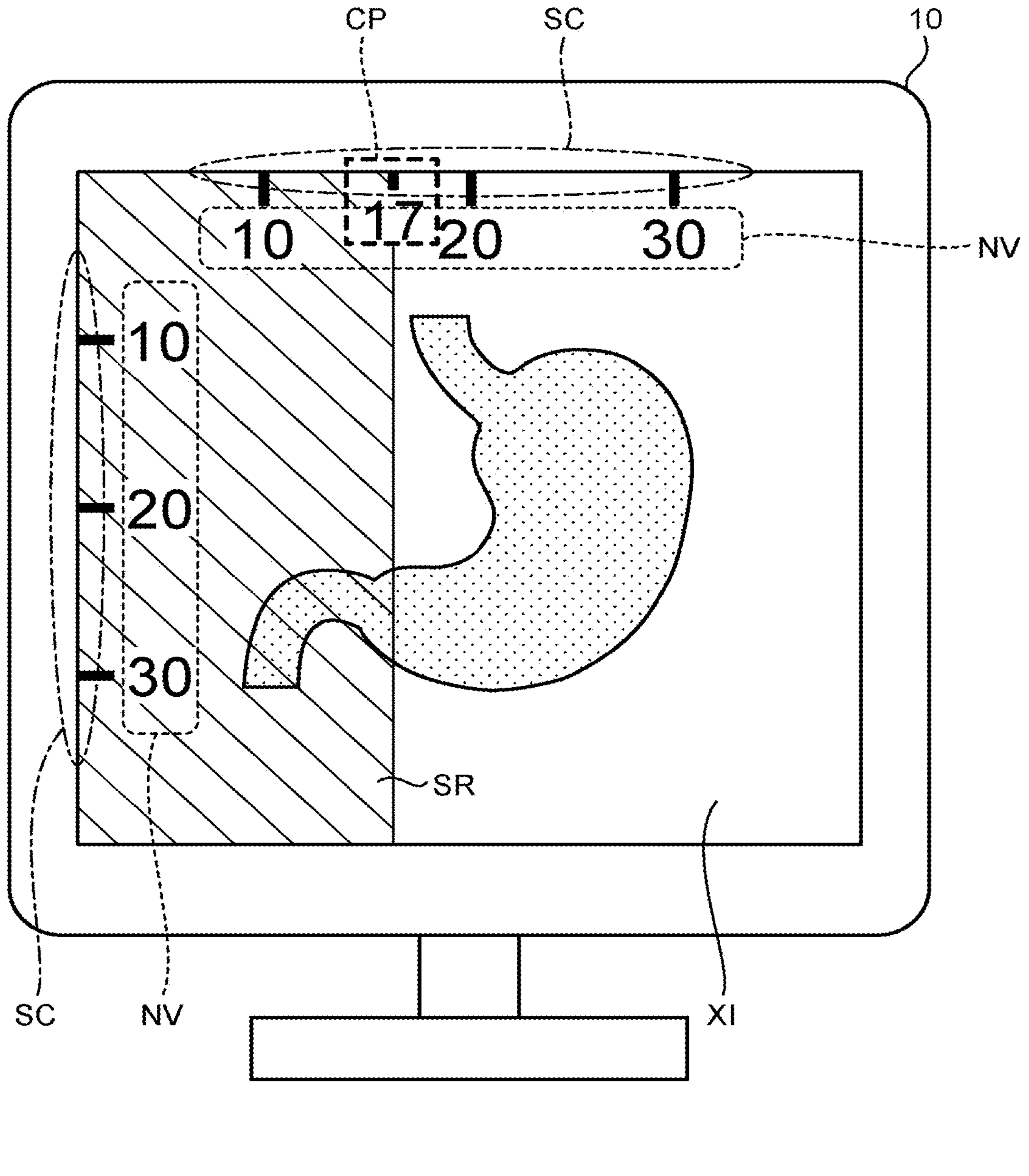
FIG. 5 illustrates one example of display of an X-ray image with numerical values and scales including a numerical value and a scale indicating the current position of a diaphragm blade according to an embodiment.
Figure 6:
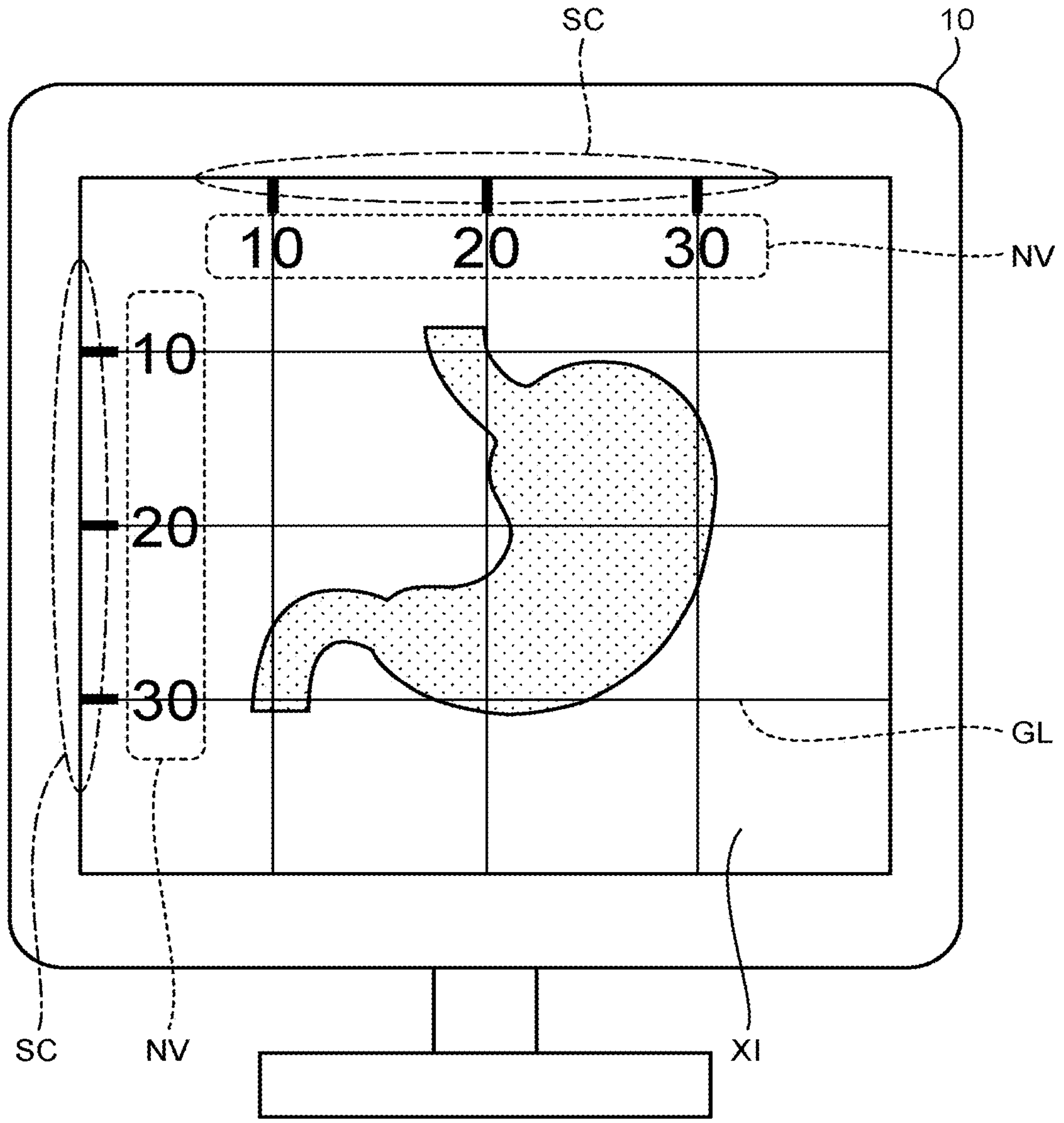
FIG. 6 illustrates one example of display of an X-ray image with numerical values, scales, and guidelines corresponding to the scales, according to an embodiment.
Figure 7:
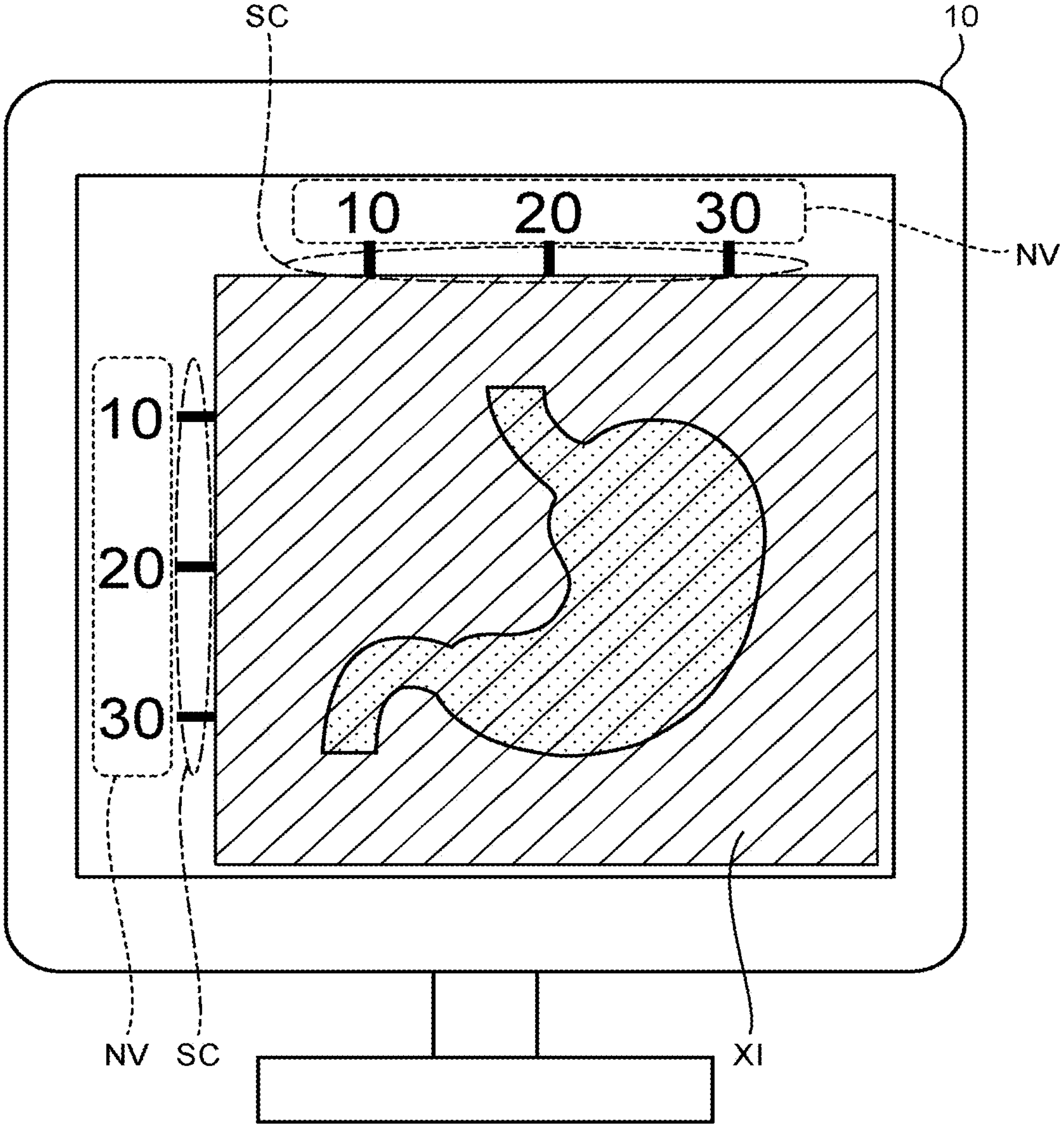
FIG. 7 illustrates one example of display of numerical values and scales in line with activation words outside the image region of an X-ray image, according to an embodiment.

The display of the numerical values NV and scales SC according to the utterance of the activation words SUW is not limited to the example shown in FIG. 4. As illustrated in FIG. 5, for example, the display unit 10 may display a numerical value CP indicating the current position of the diaphragm blade and the scale corresponding to the numerical value CP on the X-ray image XI, along with the numerical values NV and scales SC. In FIG. 5 the X-ray shielded region by the X-ray diaphragm is depicted by hatching SR. For another example, the display unit 10 may additionally display scale guidelines GL on the X-ray image XI together with the numerical values NV and scales SC, as illustrated in FIG. 6. Alternatively, responsive to the activation words, the display unit 10 may display the numerical values NV and the scales SC outside the X-ray image XI (image region), as illustrated in FIG. 7.

Step S304

When a user UR's utterance (moving instruction words) MIW with respect to the numerical values NV displayed on the display unit 10 is collected (Yes at step S304), the process proceeds to step S305. When no user UR's utterance (moving instruction words) MIW with respect to the numerical values NV displayed on the display unit 10 is collected (No at step S304), the process proceeds to step S308. The numerical value in the utterance to be collected may be a value between the numerical values NV displayed on the display unit 10, in addition to the numerical values NV displayed on the display unit 10.

Step S305

The processing circuitry 145 uses the speech recognition function 151 to recognize a numerical value from the user UR's utterance collected by the microphone 150 with respect to the numerical values NV. Specifically, the speech recognition function 151 performs speech recognition of the electric signals representing the user UR's utterance to thereby generate a diaphragm moving instruction including a recognition result indicating a diaphragm blade to be moved and the coordinate of the destination.

As illustrated in FIG. 4, the user UR has spoken "left diaphragm, 15". This diaphragm moving instruction signifies that the left-side diaphragm blade relative to the X-ray image XI is to be moved to the position indicated by the scale of 15. Namely, the coordinate of the destination of the left-side diaphragm blade is 15. The numerical value in the collected utterance may be a value between the numerical values NV displayed on the display unit 10 i.e., a value other than the scale values SC. In such a case the speech recognition function 151 may recognize the numerical value other than the scale values displayed on the display unit 10 from the user's utterance collected by the microphone 150. Thus, the speech recognition function 151 is capable of recognizing other numerical values than the numerical values NV of 10, 20, and 30 displayed as an example in FIG. 4. The speech recognition function 151 outputs the diaphragm moving instruction to the movement calculating function 153.

Step S306

The processing circuitry 145 uses the movement calculating function 153 to calculate a moving amount of the object concerned according to the diaphragm moving instruction including the recognized numerical value. For example, the movement calculating function 153 retrieves current position information of the diaphragm blade to be moved and the position-coordinate table from the memory 143. In the example of FIG. 4, the movement calculating function 153 calculates a moving amount of the left-side diaphragm blade based on the current position information of the left-side diaphragm blade, the position-coordinate table, and the coordinate (15) of the destination. That is, the movement calculating function 153 calculates a moving amount of the diaphragm blade concerned, based on the diaphragm moving instruction, the current position information of the diaphragm blade concerned, and the position-coordinate table. The movement calculating function 153 outputs the resultant moving amount of the diaphragm blade concerned to the system control unit 11.

Step S307

The system control unit 11 performs control of the imaging apparatus 110 to move the object concerned by the calculated moving amount. In the example of FIG. 4, the system control unit 11 controls the X-ray diaphragm 1*b* to move the left-side diaphragm blade to the position indicated by the scale value of 15 on the X-ray image XI. In the example of FIG. 4 the region where the diaphragm blade is moved is indicated by hatching on the X-ray image XI. In FIG. 4 the hatching SR thus indicates the region (shielded region) where the X-rays are blocked by the X-ray diaphragm. In this manner, by the user's uttering the numerical value, the diaphragm blade is placed at the position indicated by the designated numerical value on the monitor 10*d*.

Step S308

The system control unit 11 determines whether a predetermined time has passed from the display of the numerical values NV on the display unit 10. The system control unit 11 also determines whether a predetermined time has passed after controlling the imaging apparatus 110. The predetermined time is optionally settable to, for example, several seconds to over ten seconds, and preset and stored in the memory 143. After a lapse of the predetermined time from the display of the numerical values NV on the display unit 10 (Yes at step S308), the process proceeds to step S309. Unless the predetermined time has passed from the display of the numerical values NV on the display unit 10 (No at step S309), the operations at step S304 and subsequent steps are iterated.

Step S309

The system control unit 11 hides the scales SC and the numerical value NV on the X-ray image XI on display. Thus, under the control of the system control unit 11, the display unit 10 displays the X-ray image XI alone. After step S309, the operations at step S301 and subsequent steps are repeated. Specifically, after a lapse of the predetermined time from the display of the numerical values NV on the display unit 10 or upon completion of the displacement of the object concerned, the system control unit 11 hides the numerical values NV and the scales SC on the display unit 10. In other words, the scales SC and the numerical value NV are displayed on the image for a preset time, and after a lapse of the preset time, the scales SC and the numerical value NV are made hidden. In the example of FIG. 4, when the predetermined time elapses since the left-side diaphragm blade has moved to the position indicated by the scale value SC of 15, the system control unit 11 controls the display unit 10 to hide the scales SC and the numerical values NV on the X-ray image XI, for example.

Step S310

Upon completion of X-ray imaging of the subject P (Yes at step S310), the voice moving-control process ends. Unless X-ray imaging of the subject P is completed (No at step S310), the operations at step S301 and subsequent steps are iterated. The X-ray imaging is completed by a user instruction input via the input interface 141, for example.

According to the X-ray diagnosis apparatus 100 of one embodiment as described above, the imaging apparatus 110 includes the X-ray tube 1*a*, the X-ray diaphragm 1*b*, the X-ray detector unit 3, and the couch 5 to generate the X-ray image XI of the subject P by X-ray imaging. The X-ray diagnosis apparatus 100 displays the X-ray image XI with the numerical values NV indicating the positions on the X-ray image XI. The X-ray diagnosis apparatus 100 recognizes a numerical value from the collected user UR's utterance concerning the numerical values NV, to control the imaging apparatus 110 in accordance with the position (moving amount) indicated by the recognized numerical value among the numerical values NV.

According to one embodiment, for example, the X-ray diaphragm 1*b* of the X-ray diagnosis apparatus 100 includes multiple diaphragm blades. The X-ray diagnosis apparatus 100 controls the X-ray diaphragm 1*b* to move at least one of the diaphragm blades to the position corresponding to the recognized numerical value in an asymmetrical manner. Specifically, the X-ray diaphragm 1*b* of the X-ray diagnosis apparatus 100 of one embodiment includes two opposing diaphragm blades. The X-ray diagnosis apparatus 100 of one embodiment recognizes one of the two diaphragm blades from the user UR's utterance and controls the X-ray diaphragm 1*b* to move the one diaphragm blade to the position indicated by the recognized numerical value.

As such, the X-ray diagnosis apparatus 100 of one embodiment allows the user UR such as a physician to smoothly move the object concerned, e.g., diaphragm blade, to his or her intended position while treating the subject P. Owing to such features, the X-ray diagnosis apparatus 100 of one embodiment allows the user UR as a physician to restrict the irradiation range up to a limit, leaving only the region of interest as minimum required, which makes it possible to reduce radiation exposure of the subject P.

Moreover, the X-ray diaphragm 1*b* of the X-ray diagnosis apparatus 100 of one embodiment includes two opposing diaphragm blades. The X-ray diagnosis apparatus 100 of one embodiment further displays the numerical values NV corresponding to the scales SC and a numerical value and a scale representing the current position CP of the diaphragm blade. Thereby, the X-ray diagnosis apparatus 100 of one embodiment can allow the user UR to know the numerical value indicating the current position of the diaphragm blade at a glance and easily utter the position of the moving destination. In addition, by displaying the numerical values NV and the scales SC, the X-ray diagnosis apparatus 100 of one embodiment can facilitate change and control of the position of the destination, enabling the user UR to accurately move the object concerned to his or her desired position. As such, owing to the display of the numerical values NV and the scales SC, the X-ray diagnosis apparatus 100 of one embodiment can improve operability with respect to the moving of the object concerned by utterance and decrease the number of times at which the movement of the object concerned is adjusted. This leads to improving the examination throughput relative to the subject P.

Further, in response to a lapse of the predetermined time from the display of the numerical values NV on the display unit 10, the X-ray diagnosis apparatus 100 of one embodiment hides the numerical values NV on the display unit 10. As a result, by displaying the scales SC and the numerical values NV on the display unit 10 during only the voice control, the X-ray diagnosis apparatus 100 of one embodiment can prevent the scales SC and the numerical values NV on display from hindering the user UR from observing the X-ray image XI. Thereby, the X-ray diagnosis apparatus 100 of one embodiment can improve the user UR's observance of the X-ray image XI in efficiency.

Further, the X-ray diagnosis apparatus 100 of one embodiment additionally displays the scales SC corresponding to the numerical values NV and can recognize a numerical value not included in the scales SC from the user UR's utterance. In this manner the X-ray diagnosis apparatus 100 of one embodiment allows designation of numerical values not included in the scales.

Further, the X-ray diagnosis apparatus 100 of one embodiment additionally displays the scales SC corresponding to the numerical values NV and the guidelines GL corresponding to the scales SC. Thereby, the X-ray diagnosis apparatus 100 of one embodiment can allow the user UR to know, at a glance, the numerical value indicating the position of the destination of the object concerned, improving the user UR's convenience of uttering the numerical value.

Further, the X-ray diagnosis apparatus 100 of one embodiment can display the numerical values NV outside the X-ray image. Owing to the display of the numerical values NV outside the X-ray image, the X-ray diagnosis apparatus 100 of one embodiment can prevent the scales SC and the numerical values NV from disturbing the user UR's observance of the X-ray image XI. Consequently, the X-ray diagnosis apparatus 100 of one embodiment can improve the user UR's observance of the X-ray image XI in efficiency.

As such, the X-ray diagnosis apparatus 100 of one embodiment can allow the user UR being a physician to smoothly move the imaging apparatus 110 to his or her intended position even while his or her hands are being occupied with something else.

First Modification

Figure 8:
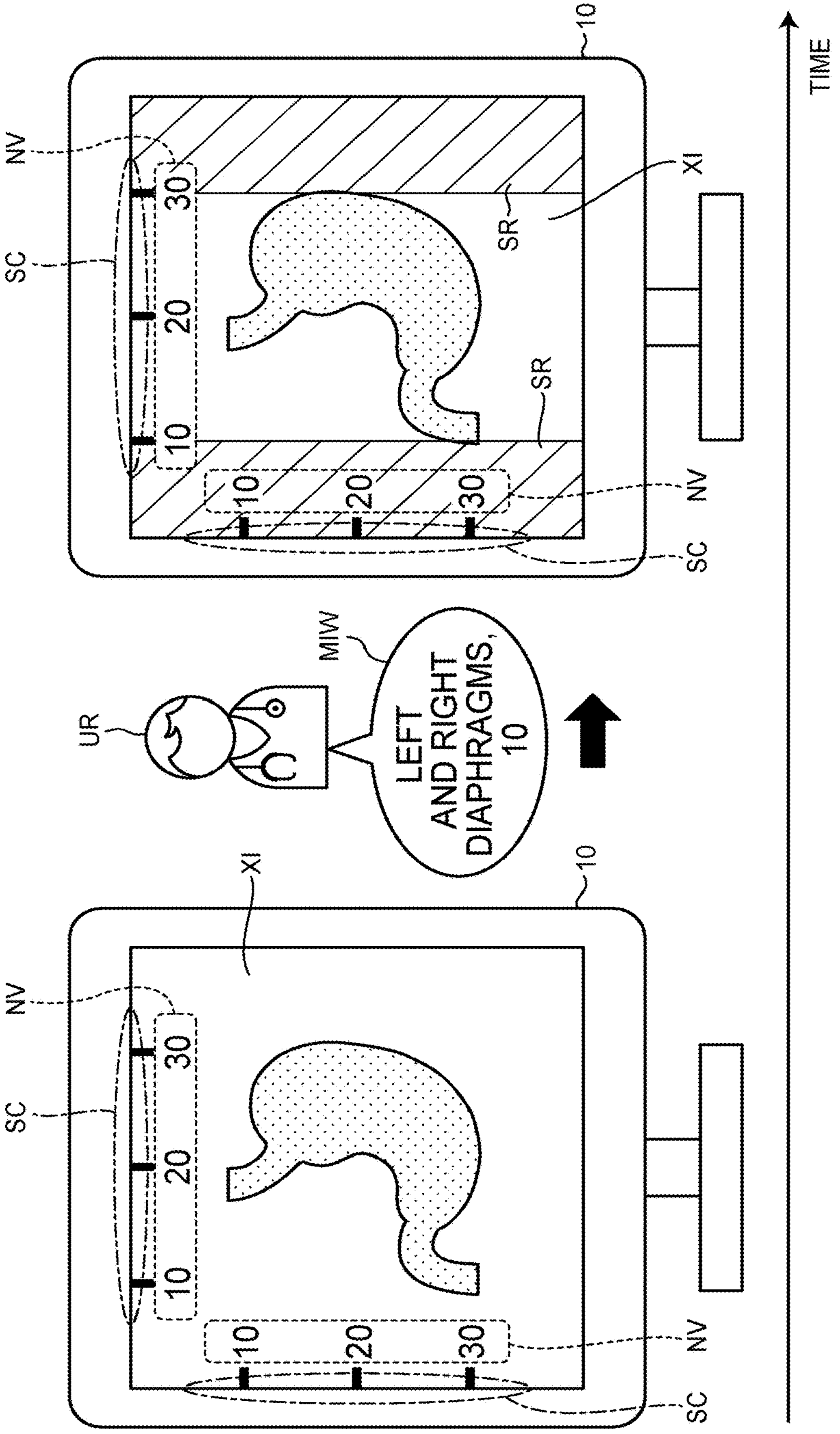
FIG. 8 illustrates an outline of a voice moving-control procedure according to a first modification of some embodiments by way of example.

A first modification involves symmetrically moving two opposing diaphragm blades by voice control. Thus, an object to be controlled by the voice moving-control process is two opposing diaphragm blades of the X-ray diaphragm 1*b*. FIG. 8 depicts an outline of the voice moving-control process according to the first modification, as an example.

In the first modification, after uttering "diaphragm, voice control", the user UR utters the locations of the diaphragm blades to be moved and numerical values indicating the coordinates of the destinations of the diaphragm blades. The locations of the diaphragm blades to be moved are the locations of a vertical or horizontal diaphragm blade pair relative to the X-ray image XI displayed on the display unit 10. The numerical values indicating the coordinates of the destinations of the diaphragm blades are numerical values (coordinate values) displayed on the display unit 10, as in some embodiments.

To move a left one of the two diaphragm blades relative to the X-ray image XI to the numerical value of 10 and a right one to the numerical value of 30, for example, the user UR may utter "left and right diaphragms, 10" to designate the locations of the diaphragm blades to be moved and the numerical value indicating the coordinates of the destinations thereof. In this case, the utterance signifies that the left-side diaphragm blade is moved to the coordinate of 10 and the right-side diaphragm blade is moved to the coordinate of 30 on the X-ray image XI on display. The utterance of the locations of the diaphragm blades to be moved and the numerical value indicating the coordinates of the destinations of the diaphragm blades is not limited to “left and right diaphragms, 10”, and may be a different utterance, e.g., “10, left and right diaphragms”.

The microphone 150 collects and converts moving instruction words MIW to electric signals for output to the remote operator station 130. The speech recognition function 151 recognizes the two diaphragm blades from the user UR’s utterance, i.e., the moving instruction words MIW. Specifically, the speech recognition function 151 recognizes the locations of the diaphragm blades to be controlled by the voice moving-control process and the numerical value indicating the coordinates of the destinations from the user UR’s utterance of the moving instruction words MIW. The speech recognition function 151 then outputs the diaphragm moving instruction to the movement calculating function 153.

The processing circuitry 145 uses the movement calculating function 153 to calculate a moving amount of the objects concerned based on the diaphragm moving instruction. The movement calculating function 153’s moving-amount calculation is the same as or similar to that in some embodiments, therefore, a description thereof is omitted. The system control unit 11 moves the objects concerned (e.g., two opposing diaphragm blades) by the calculated moving amount.
In other words, the system control unit 11 controls the X-ray diaphragm 1*b* to symmetrically move the two diaphragm blades to the positions indicated by the recognized numerical value, as illustrated in FIG. 8. In FIG. 8 the regions (shielded region) where the X-rays are blocked by the X-ray diaphragm 1*b* is indicated by hatching SR. The voice moving-control process of the first modification is the same as or similar to that in some embodiments except for the user UR’s utterance and the object to be controlled at step S304 of FIG. 3, therefore, a description thereof is omitted.

According to the first modification, the X-ray diaphragm 1*b* of the X-ray diagnosis apparatus 100 includes the two opposing diaphragm blades, and the X-ray diagnosis apparatus 100 can recognize the two opposing diaphragm blades from the user UR’s utterance to control the X-ray diaphragm 1*b* to symmetrically move the two opposing diaphragm blades to the positions indicated by the numerical value. Consequently, the X-ray diagnosis apparatus 100 of the first modification can symmetrically move the two opposing diaphragm blades with easiness according to the user UR’s utterance, thereby improving the operability of the diaphragm control. The rest of the effects are the same as or similar to those of the embodiments, therefore, a description thereof is omitted.

Second Modification

Figure 9:
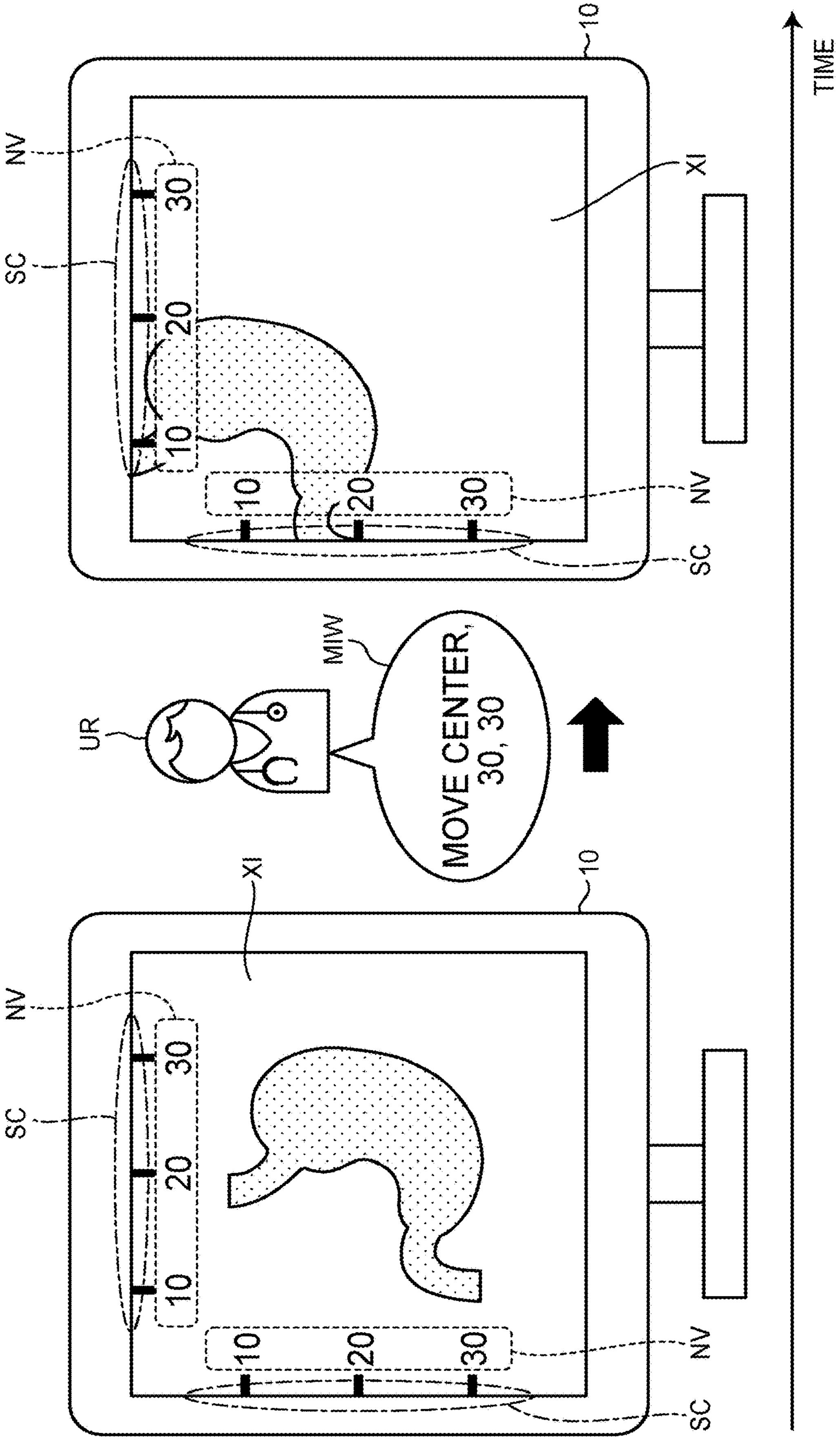
FIG. 9 illustrates an outline of a voice moving-control procedure according to a second modification of some embodiments by way of example.

A second modification involves independently controlling the multiple diaphragm blades to move the center of the X-ray irradiation range by voice. In other words, the multiple diaphragm blades are controlled to move in an asymmetric manner in order to move the center of the X-ray image XI. Thus, in the second modification the multiple diaphragm blades are independently moved to move the center of the X-ray image XI. FIG. 9 depicts an outline of the voice moving-control process according to the second modification, as an example.

In the second modification, after uttering “diaphragm, voice control”, the user UR utters the coordinates (e.g., in order of x-coordinate and y-coordinate) of the center of the destination on the X-ray image XI. As illustrated in FIG. 9, for example, to set the position coordinates (30, 30) of the center of the X-ray image XI before moving the center to those of the center in the next X-ray imaging, the utterance designating the position coordinates of the center may be, for example, “move the center, 30, 30”. The utterance designating the position coordinates of the center may be a different utterance such as “30, 30, move the center”, in addition to “move the center, 30, 30”.

The microphone 150 collects and converts the moving instruction words MIW into electric signals for output to the remote operator station 130. The speech recognition function 151 recognizes the numerical values indicating the center of the X-ray irradiation range from the user UR’s utterance, i.e., the moving instruction words MIW. The speech recognition function 151 then outputs the coordinates of the center as the diaphragm moving instruction to the movement calculating function 153.

The processing circuitry 145 uses the movement calculating function 153 to calculate a moving amount of each of the diaphragm blades based on the diaphragm moving instruction. The movement calculating function 153’s moving-amount calculation is the same as or similar to that in the embodiments, therefore, a description thereof is omitted. The system control unit 11 moves the diaphragm blades concerned by the calculated moving amounts. In other words, the system control unit 11 controls the X-ray diaphragm 1*b* to independently (asymmetrically) move the two diaphragm blades such that the position indicated by the recognized numerical values (coordinates of the center) matches the center of the X-ray irradiation range, as illustrated in FIG. 9.

According to the second modification as illustrated in FIG. 9, the position of the viewing field can be moved without a change of the viewing field size. In other words, the voice moving-control process of the second modification is to change the center of the X-ray image XI while maintaining the viewing field size, i.e., moving the X-ray irradiation range in parallel, following the user UR’s utterance (coordinates). The voice moving-control process of the second modification is the same as or similar to that in the embodiments except for the user UR’s utterance and the object to be controlled at step S304 of FIG. 3, therefore, a description thereof is omitted.

According to the second modification, the X-ray diagnosis apparatus 100 can recognize the numerical values indicating the center of the X-ray irradiation range from the user UR’s utterance, to control the X-ray diaphragm 1*b* to independently move the diaphragm blades to set the center of the X-ray irradiation range at the position indicated by the recognized numerical values. Thereby, the X-ray diagnosis apparatus 100 of the second modification can asymmetrically move the diaphragm blades according to the user UR’s utterance to change the center of the X-ray image XI while maintaining the viewing field size. In other words, the X-ray diagnosis apparatus 100 of the second modification can allow the user to operate the diaphragm blades by inputting the coordinates by voice such that the position indicated by the coordinates matches the image center. Thus, the X-ray diagnosis apparatus 100 of the second modification can allow the user to change the viewing field position without a change of the viewing field size. The rest of the effects are the same as or similar to those of the first modification, therefore, a description thereof is omitted.

Third Modification

Figure 10:
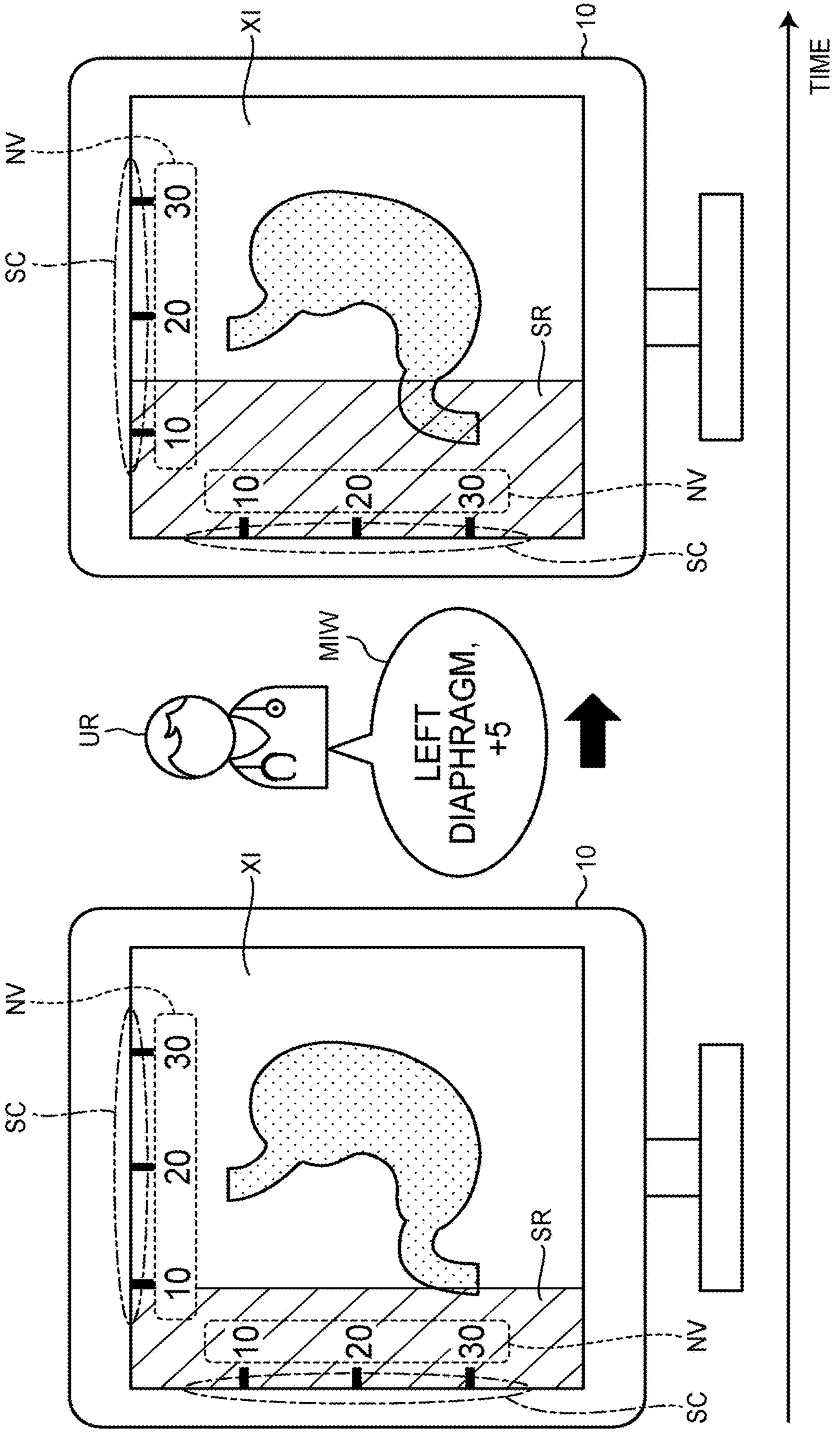
FIG. 10 illustrates an outline of a voice moving-control procedure according to a third modification of some embodiments by way of example.

A third modification involves vocal designation of the numerical value using not the absolute value but a relative value with respect to the current position (defined as zero) of an object to be controlled (for example, diaphragm blade). In the third modification, the user UR utters words including a relative value, unlike in the embodiments. The relative value is a value with a plus symbol (+) or a minus symbol (−) added. The plus symbol represents a rightward direction relative to the X-ray image XI while the minus symbol represents a leftward direction relative to the X-ray image XI, for example. The relative value thus represents a diaphragm moving amount on the X-ray image XI. FIG. 10 depicts an outline of the voice moving-control process according to the third modification, as an example.

In the third modification, after uttering "diaphragm, voice control", the user UR utters the location of the diaphragm blade to be moved and a numerical value (relative value) indicating the relative position of the destination of the diaphragm blade. The locations of the diaphragm blades to be moved are top, bottom, right, and left on the X-ray image displayed on the display unit 10. The numerical values indicating the relative positions of the destinations of the diaphragm blades are relative values to the numerical values (coordinate values) displayed on the display unit 10. Namely, the coordinate of the destination represents a value resulting from addition or subtraction of the relative value to or from the current position of the object to be controlled (e.g., diaphragm blade).

As an example, to move rightward a left one of a diaphragm blade pair horizontal to the X-ray image XI by 5, the utterance of the location of the diaphragm blade to move and the relative value may be "left diaphragm, +5", as illustrated in FIG. 10. In FIG. 10 the coordinate of the current position of the left-side diaphragm blade is, for example, set to 10, and the utterance denotes moving the left-side diaphragm blade relative to the X-ray image XI to the coordinate of 10+5 displayed on the X-ray image XI. The utterance designating the location of the diaphragm blade to move and the numerical value indicating the coordinate of the destination of the diaphragm blade may be a different utterance such as "+5, left diaphragm", in addition to "left diaphragm, +5".

The microphone 150 collects and converts the moving instruction words MIW into electric signals for output to the remote operator station 130. For example, the microphone 150 collects the user UR's utterance containing a relative value to the current position of the diaphragm blade. The speech recognition function 151 recognizes the diaphragm blade to be moved from the user UR's utterance, i.e., the moving instruction words MIW. Specifically, the speech recognition function 151 recognizes the location of the diaphragm blade to be controlled by the voice moving-control process and the relative value of the destination of the diaphragm blade from the user UR's moving instruction words MIW. The speech recognition function 151 then outputs a diaphragm moving instruction to the movement calculating function 153.

The processing circuitry 145 uses the movement calculating function 153 to calculate a moving amount of the object concerned based on the diaphragm moving instruction. The movement calculating function 153's moving-amount calculation is the same as or similar to that in the embodiments, therefore, a description thereof is omitted. The system control unit 11 moves the diaphragm blade concerned by the calculated moving amount. In other words, the system control unit 11 controls the X-ray diaphragm 1*b* to move the diaphragm blade concerned to the position indicated by the recognized relative value, as illustrated in FIG. 10. In FIG. 10, the regions (shielded region) where the X-rays are blocked by the X-ray diaphragm is indicated by hatching SR. The voice moving-control process of the third modification is the same as or similar to that in the embodiments except for the user UR's utterance at step S304 of FIG. 3, therefore, a description thereof is omitted.

According to the X-ray diagnosis apparatus 100 of the third modification, the microphone 150 collects the user UR's utterance including the relative value to the current position of the diaphragm blade. Thereby, the X-ray diagnosis apparatus 100 of the third modification can allow the user UR to vocally designate the moving destination of the diaphragm blade more easily, improving the operability of the diaphragm control. The rest of the effects are the same as or similar to those in the embodiments, therefore, a description thereof is omitted.

Fourth Modification

Figure 11:
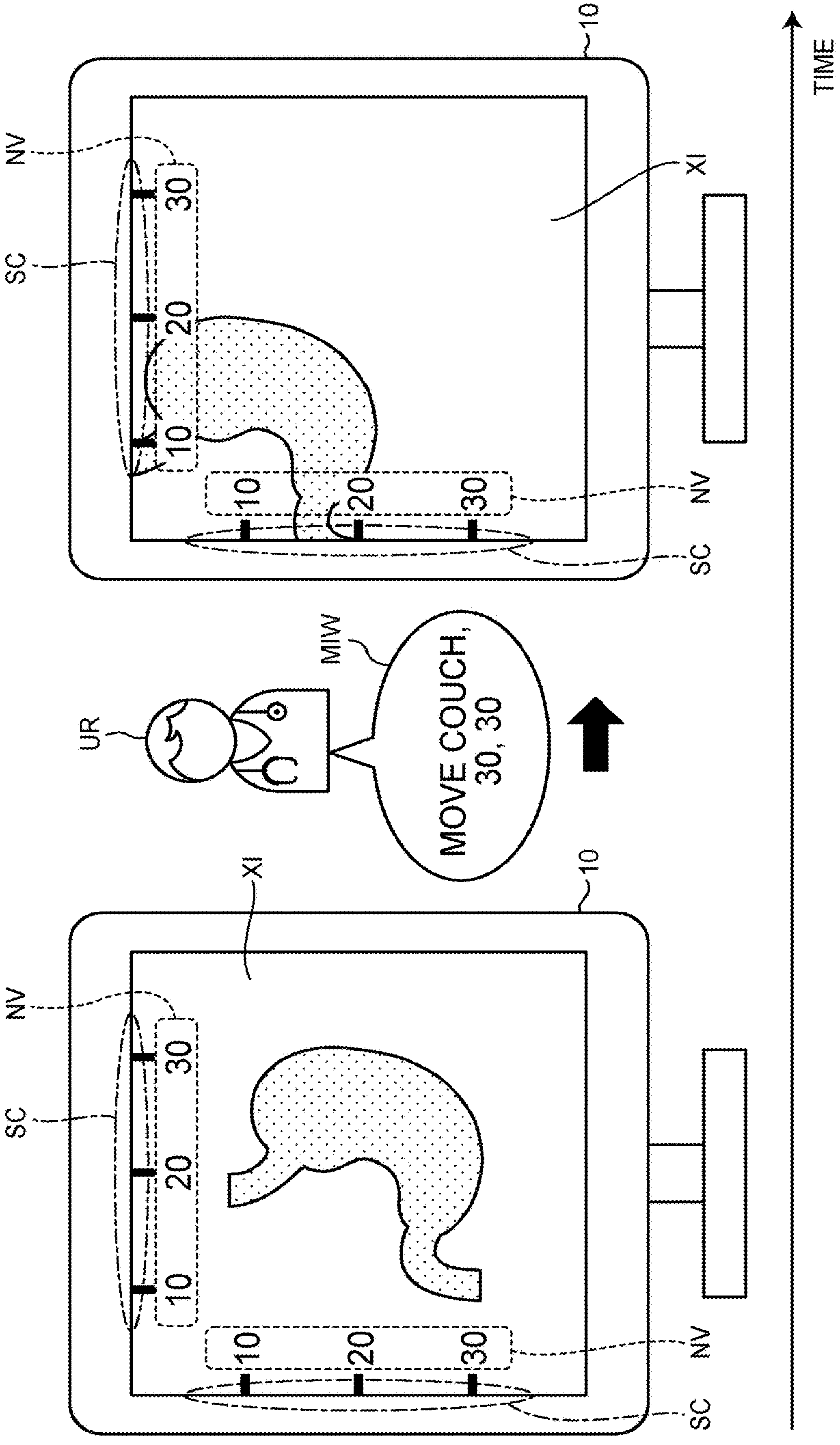
FIG. 11 illustrates an outline of a voice moving-control procedure according to a fourth modification of some embodiments by way of example.

A fourth modification involves setting the couch 5 as an object to be controlled. The system control unit 11 thus controls the couch 5 to be moved to the position indicated by the recognized numerical value. FIG. 11 depicts an outline of the voice moving-control process according to the fourth modification, as an example. In the fourth modification, the user UR utters "couch, voice control" as activation words, for example. The activation words to initiate the voice moving-control process are not limited to the "couch, voice control" and may be any other words such as "voice control, couch" as long as the utterance conveys an intention to vocally operate the couch 5. In addition, such an utterance may be, for example, related to the words contained in a physician's instruction for a technician to operate the couch 5. The voice moving-control process in the fourth modification controls the movement of the couch 5. For this purpose, the current position information as to the couch 5 is updated appropriately in accordance with X-ray imaging of the subject P and stored in the memory 143.

According to the fourth modification, the user UR utters the coordinates (e.g., in order of x-coordinate and y-coordinate) of the center of the destination on the X-ray image XI after uttering the words "couch, voice control". As illustrated in FIG. 11, for example, to set the position coordinates (30, 30) of the center of the X-ray image XI before moving the center to those of the center in the next X-ray imaging, the utterance designating the position coordinates of the center may be, for example, "move the couch, 30, 30". The utterance designating the position coordinates of the center may be a different utterance such as "30, 30, move the couch", in addition to "move the couch, 30, 30".

The microphone 150 collects and converts moving instruction words MIW into electric signals for output to the remote operator station 130. The speech recognition function 151 recognizes the numerical values indicating the center of the X-ray irradiation range from the user UR's utterance, i.e., the moving instruction words MIW. The speech recognition function 151 then outputs the coordinates indicating the center as a couch moving instruction to the movement calculating function 153.

Triggered by receipt of the couch moving instruction, the processing circuitry 145 uses the movement calculating function 153 to obtain current position information of the couch 5 to be moved and the position-coordinate table from the memory 143. The movement calculating function 153 then calculates a moving amount of the couch 5 using the current position information, the position-coordinate table, and the coordinates of the destination (center). The movement calculating function 153 outputs the resultant moving amount to the system control unit 11. The system control unit 11 then moves the couch 5 by the calculated moving amount. In other words, the system control unit 11 controls the couch 5 to be moved to the position (coordinates of the destination of the object concerned) indicated by the recognized numerical values among the numerical values displayed with the X-ray image on the display unit 10. Thus, the system control unit 11 controls the couch 5 such that the position indicated by the recognized numerical values coincides with the center of irradiation range.

According to the fourth modification as illustrated in FIG. 11, the position of the viewing field can be moved without a change of the viewing field size. In other words, the voice moving-control process of the fourth modification is to change the center of the X-ray image XI while maintaining the viewing field size, i.e., moving the X-ray irradiation range in parallel by moving the couch 5, following the user UR's utterance (coordinates). The voice moving-control process of the fourth modification is the same as or similar to that in the second modification and the embodiments except for the user UR's utterance (activation words) and the object to be controlled at step S304 of FIG. 3. Thus, according to the fourth modification it is made possible to generate X-ray images XI same as or similar to those in the second modification by moving the couch 5, while the diaphragm opening set by the diaphragm blades and the positions of the diaphragm blades remain unchanged. For this reason, a description of the voice moving-control process in the fourth modification is omitted.

According to the fourth modification, the X-ray diagnosis apparatus 100 can control the couch 5 to be moved to the position indicated by the numerical values recognized by the speech recognition function 151. Specifically, the X-ray diagnosis apparatus 100 of the fourth modification recognizes the numerical values indicating the center of the X-ray irradiation range from the user UR's utterance, to control the couch 5 such that the position indicated by the recognized numerical values coincides with the center of the X-ray irradiation range. Thereby, the X-ray diagnosis apparatus 100 of the fourth modification can move the couch 5, following the user UR's utterance, to change the center of the X-ray image XI while maintaining the viewing field size without moving the diaphragm blades. As such, the X-ray diagnosis apparatus 100 of the fourth modification can allow the user to vocally control the couch 5 to be moved to his or her intended position. Thus, the X-ray diagnosis apparatus 100 of the fourth modification can allow the user to operate the couch 5 by inputting coordinates by voice such that the position indicated by the coordinates matches the image center. The rest of the effects are the same as or similar to those of the embodiments and the second modification, therefore, a description thereof is omitted.

Fifth Modification

Figure 12:
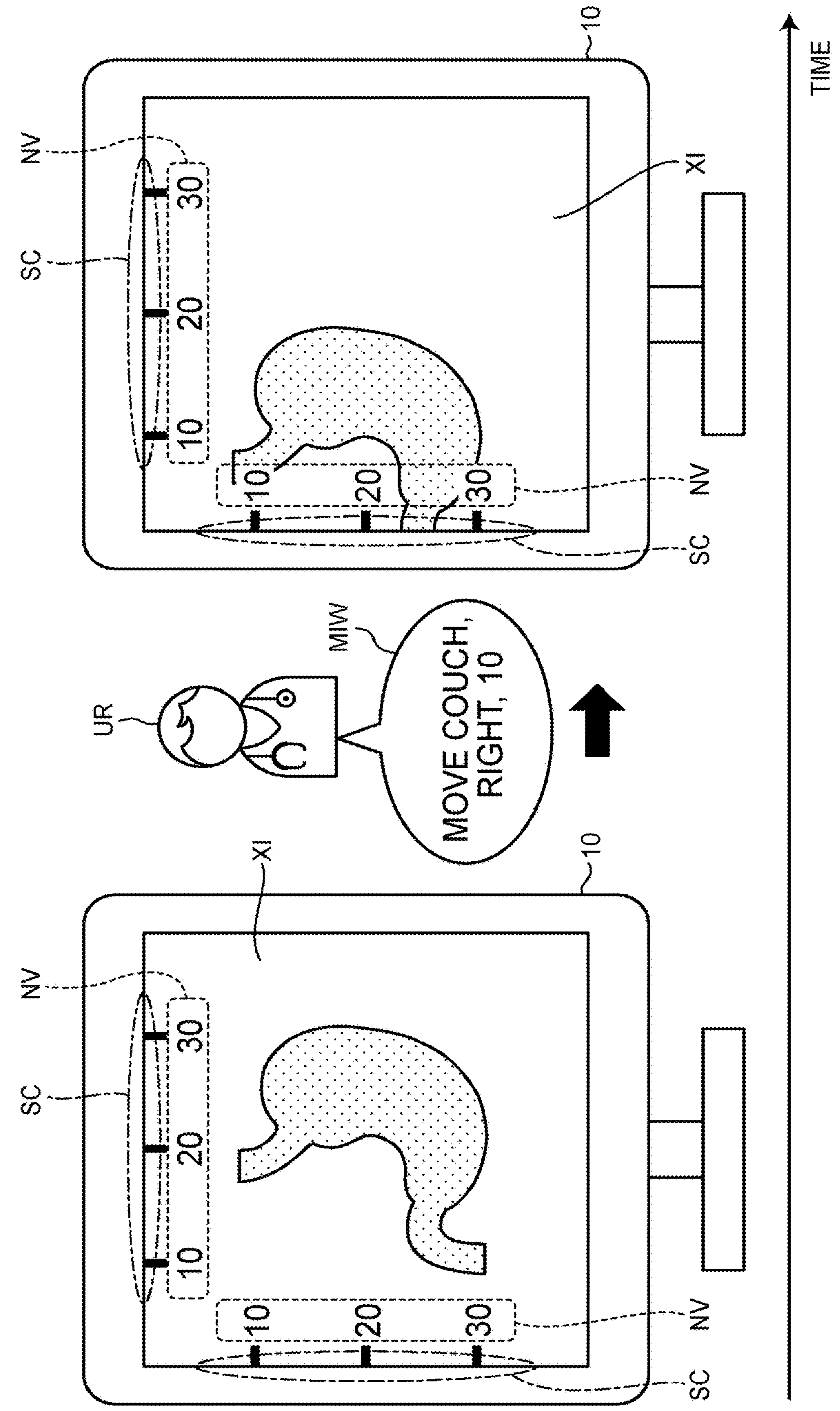
FIG. 12 illustrates an outline of a voice moving-control procedure according to a fifth modification of some embodiments by way of example.

A fifth modification involves vocally designating the numerical value using not the absolute value but a relative value with respect to the current position (defined as zero) of the couch 5 to be controlled. In the fifth modification, thus, the user UR utters words including a relative value, unlike in the embodiments. A moving direction of the couch 5 and a moving amount of the couch 5 on the X-ray image XI are added to the relative value. FIG. 12 depicts an outline of the voice moving-control process according to the fifth modification, as an example.

According to the fifth modification, after uttering "couch, voice control", the user UR utters an object to be moved (couch 5) and a numerical value (relative value) indicating the position of the destination of the couch 5. That is, the user's utterance contains a relative value to the current position of the couch 5. The numerical value indicating the position of the destination of the couch 5 is a value relative to the numerical values (coordinate values) displayed on the display unit 10. Thus, the coordinate of the destination represents a value resulting from adding or subtracting the relative value to or from the current position of the couch 5 to be controlled.

For example, to move the couch 5 rightward by 10 relative to the X-ray image XI, the utterance may be "move the couch, right, 10" to designate an object to be moved and a relative value. The utterance to designate an object to be moved and a relative value may be a different utterance, e.g., "right, 10, move the couch" in addition to "move the couch, right, 10".

The microphone 150 collects and converts moving instruction words MIW into electric signals for output to the remote operator station 130. The user UR's utterance collected by the microphone 150 includes, for example, a relative value to the current position of the couch 5. The speech recognition function 151 recognizes the relative value indicating the destination of the couch 5 to be moved by the voice moving-control process from the user UR's utterance, i.e., the moving instruction words MIW. The speech recognition function 151 then outputs a couch moving instruction to the movement calculating function 153.

The processing circuitry 145 uses the movement calculating function 153 to calculate a moving amount of the couch 5 according to the couch moving instruction. The movement calculating function 153's moving-amount calculation is the same as or similar to that in the embodiments, therefore, a description thereof is omitted. The system control unit 11 then moves the couch 5 by the calculated moving amount. In other words, the system control unit 11 controls the couch 5 to be moved to the position of the destination indicated by the recognized relative value, as illustrated in FIG. 12. The voice moving-control process of the fifth modification is the same as or similar to that in the embodiments except for the user UR's utterance (activation words) and the object to be controlled at step S304 of FIG. 3, therefore, a description thereof is omitted.

According to the X-ray diagnosis apparatus 100 of the fifth modification, the microphone 150 collects the user UR's utterance of the relative value to the current position of the couch 5. As such, the X-ray diagnosis apparatus 100 of the fifth modification can allow the user UR to more simply designate the destination of the couch 5 by voice, leading to improving the operability of the moving control over the couch 5. The rest of the effects are the same as or similar to those in the embodiments, therefore, a description thereof is omitted.

Sixth Modification

The embodiments and first to fifth modifications use different activation words for moving the diaphragm blade or blades and the couch 5. In the sixth modification, however, the same activation words, e.g., "voice moving control" are used. Thus, the user UR's utterance at step S304 includes a numerical value and the name of an object to be moved (e.g., the diaphragm blade or couch 5). When the user UR's utterance includes no name of an object to be moved at step S304, the system control unit 11 temporarily stops performing the voice moving-control process to the imaging apparatus 110. The system control unit 11 then issues a predetermined alarm, e.g., "Please speak an object to be moved" by voice.

According to the sixth modification, it is possible to facilitate the initiation of the voice moving-control process by simplifying the activation words, to be able to improve the examination throughput relative to the subject P.

Seventh Modification

A seventh modification involves performing predetermined image processing to a region of interest (ROI) designated by the user's utterance on the X-ray image XI. In the seventh modification the predetermined image processing is defined as enlargement of the ROI on display. The activation words for initiating the image processing in the seventh modification are defined as "enlarge, voice control", for example. In addition to "enlarge, voice control", the activation words related to the voice-initiated image processing (hereinafter, voice-controlled image processing) may be any other words such as "voice control, enlarge" as long as the words denote an intention to perform voice-controlled image processing. Other words may include, for example, a term associated with words used in a physician's instruction for a technician to designate or enlarge an ROI.

In response to the user UR's utterance, the microphone 150 collects the words denoting execution of image processing (for example, "enlarge, voice control"). The processing circuitry 145 uses the speech recognition function 151 to recognize from the user's utterance that voice-controlled image processing is to be performed. In the seventh modification, after uttering "enlarge, voice control", the user UR utters numerical values indicating the coordinates of the center of the ROI to be enlarged on the X-ray image XI or numerical values indicating two coordinates of two endpoints of a diagonal line of an ROI if the ROI is rectangular. The numerical values may represent four coordinates other than one or two coordinates.

The microphone 150 collects and converts the utterance of the numerical value (hereinafter, processing region words) to electric signals for output to the processing circuitry 145. The processing circuitry 145 uses the speech recognition function 151 to perform speech recognition of the electric signals and recognize the numerical value. The speech recognition function 151 outputs the numerical value to the system control unit 11.

The system control unit 11 uses the setting function 111 to set a region of interest (ROI) on the X-ray image XI based on the recognized numerical value. When the numerical values correspond to the coordinates of the center of the ROI to be enlarged, the setting function 111 retrieves a predetermined region from the memory 143. The predetermined region has a scale factor relative to an ROI size or a preset longitudinal and lateral size. The predetermined region may be referred to as a predetermined scale factor. The predetermined region is appropriately changeable by a user's instruction given via the input interface 141.

The setting function 111 sets a predetermined region centered around the numerical values on the X-ray image XI as an ROI. Specifically, when the numerical values recognized by the speech recognition function 151 represent one coordinate, the setting function 111 sets a predetermined region centered around the coordinate as an ROI. When the numerical values represent two coordinates, the setting function 111 sets, as an ROI, a rectangular region with the apexes of a diagonal line at the two coordinates. In other words, the setting function 111 sets a rectangular region having a diagonal line connecting the two coordinates as a region of interest (ROI).

The system control unit 11 uses the image processing function 113 to perform the predetermined image processing to the region of interest. Specifically, the image processing function 113 generates an enlarged image by enlarging the ROI to the image region of the display unit 10. Thus, the image processing function 113 generates an enlarged image of the set ROI through the predetermined image processing. The display unit 10 displays an X-ray image having undergone the image processing. Specifically, the display unit 10 replaces the X-ray image with the enlarged image on display. As such, in the seventh modification, in response to the user UR's vocal designation of the ROI, the ROI is enlarged on display. In response to a vocal designation of one coordinate, for example, the ROI is enlarged on display such that the designated coordinate matches the center of the predetermined region on the screen.

As configured above, in response to a user's utterance of the activation words, the X-ray diagnosis apparatus 100 of the seventh modification displays an X-ray image with the numerical values of a coordinate system and the scales, and performs an ROI enlargement process (hereinafter, voice-controlled image processing) in response to a user's utterance of voice enlargement control. Steps of the voice-controlled image processing will be described below with reference to FIG. 13.

Figure 13:
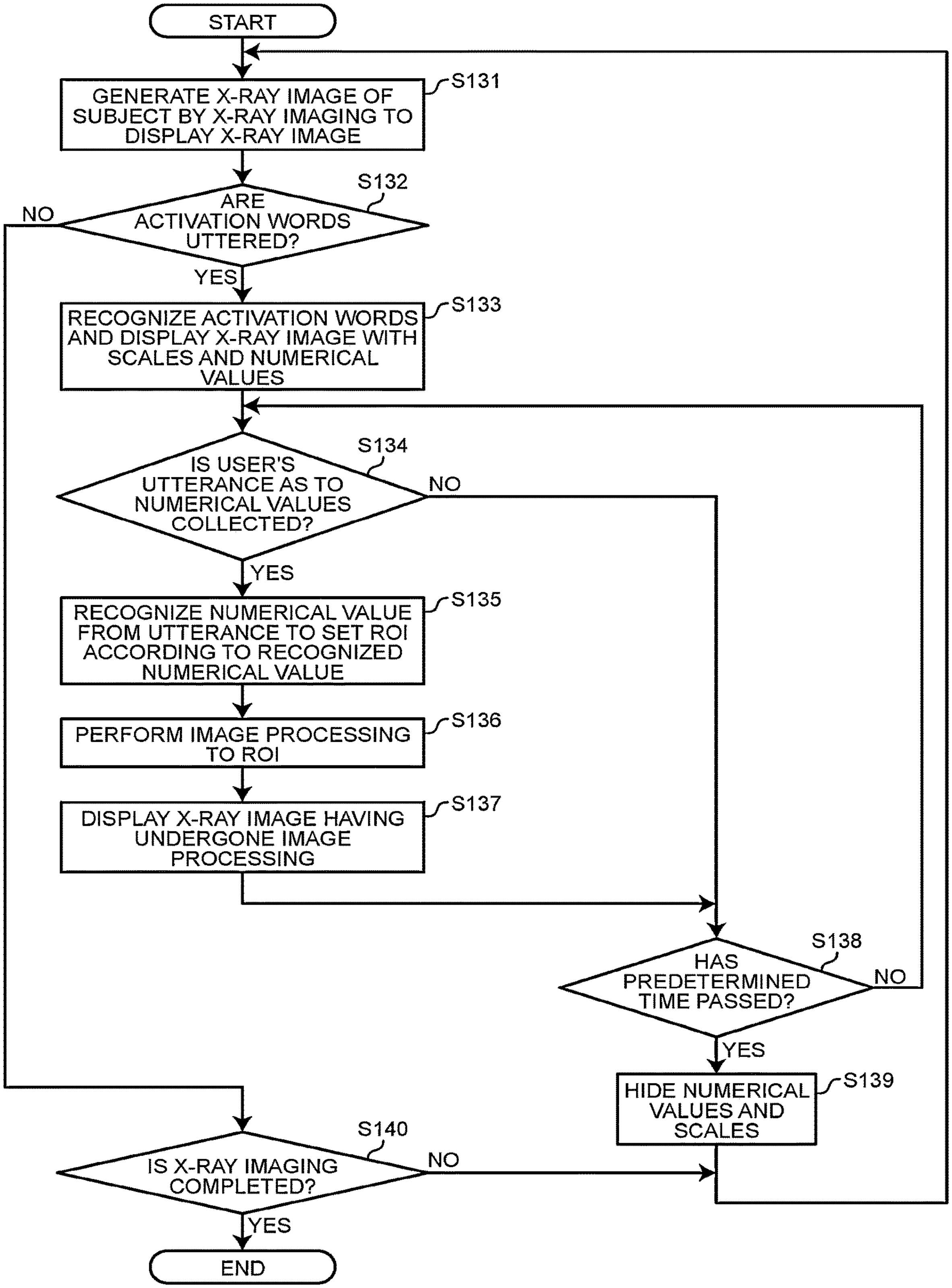
FIG. 13 is a flowchart illustrating an outline of a voice moving-control procedure according to a seventh modification of some embodiments by way of example.

FIG. 13 is a flowchart illustrating an outline of the voice-controlled image processing by way of example. In the seventh modification, the voice-controlled image processing is exemplified by an ROI enlargement process, as described above. The details of the enlargement process can be set by any of known methods, therefore, a description thereof is omitted. Another type of image processing will be explained later as an exemplary modification.

Voice-Controlled Image Processing

Step S131

The imaging apparatus 110 generates an X-ray image XI of the subject P by irradiating the subject P with X-rays. The display unit 10 displays the X-ray image XI.

Step S132

The microphone 150 collects an utterance of the activation words, e.g., "enlarge, voice control", when issued by the user UR (Yes at step S132). The microphone 150 converts the utterance into electric signals for output to the remote operator station 130. The process then proceeds to step S133. Without the user UR's utterance of the activation words (No step S132), the process proceeds to step S140.

Step S133

The processing circuitry 145 uses the speech recognition function 151 to recognize the activation words. Thereby, the speech recognition function 151 specifies the type of image processing in the voice-controlled image processing. According to the seventh modification, the speech recognition function 151 specifies the type of image processing (enlargement in this modification) with respect to the ROI through the activation-word recognition. In response to the recognized activation words, the system control unit 11 displays the X-ray image XI with multiple numerical values NV indicating the positions on the X-ray image XI on the display unit 10. The display unit 10 may additionally display multiple scales corresponding to the numerical values NV.

Step S134

When the user UR's utterance relative to the numerical values NV (processing region words) displayed on the display unit 10 is collected (Yes at step S133), the process proceeds to step S135. With no collected user UR's utterance relative to the numerical values NV (processing region words) displayed on the display unit 10 (No at step S134), the process proceeds to step S138. The numerical value contained in the collected utterance is not limited to the numerical values NV displayed on the display unit 10 and may be a value among the numerical values NV displayed on the display unit 10.

Step S135

The processing circuitry 145 uses the speech recognition function 151 to recognize the numerical value from the user UR's utterance relative to the numerical values NV collected by the microphone 150. Specifically, the speech recognition function 151 specifies the coordinates for use in image processing through speech recognition of the electric signals representing the user UR's utterance. The system control unit 11 uses the setting function 111 to set an ROI on the X-ray image XI based on the recognized numerical value.

Step S136

The system control unit 11 uses the image processing function 113 to perform image processing to the ROI. Specifically, the image processing function 113 enlarges the ROI of the X-ray image XI to the image region of the display unit 10. The image processing function 113 generates an enlarged image of the ROI through the ROI enlargement process.

Step S137

The system control unit 11 displays the X-ray image (enlarged image in this modification) having undergone the image processing on the display unit 10. Namely, the display unit 10 displays the enlarged image under the control of the system control unit 11.

Step S138

The system control unit 11 determines whether a predetermined time has passed from the display of the multiple numerical values NV on the display unit 10. The system control unit 11 also determines whether a predetermined time has passed from the display of the X-ray image having undergone the image processing. With a lapse of the predetermined time from the display of the multiple numerical values NV on the display unit 10 (Yes at step S138), the process proceeds to step S139. Before a lapse of the predetermined time from the display of the multiple numerical values NV on the display unit 10 (No at step S138), the operations at step S134 and subsequent steps are iterated.

Step S139

The system control unit 11 hides the scales SC and the numerical values NV displayed with the X-ray image XI on display. The operation at step S139 is similar to that at step S309, therefore, a description thereof is omitted.

Step S140

As X-ray imaging of the subject P completes (Yes at step S140), the voice-controlled image processing ends. Unless X-ray imaging of the subject P completes (No at step S140), the operations at step S131 and subsequent steps are iterated. The X-ray imaging is completed by a user instruction input via the input interface 141, for example.

According to the seventh modification of the embodiments as described above, the X-ray diagnosis apparatus 100 sets a region of interest (ROI) on the X-ray image XI with reference to the numerical values recognized by the speech recognition function 151, performs predetermined image processing to the region of interest (ROI), and display an X-ray image having undergone the image processing. Specifically, the X-ray diagnosis apparatus 100 according to the seventh modification of the embodiments sets a predetermined region centered around a single coordinate as a region of interest (ROI) when the numerical values indicate a single coordinate. When the numerical values indicate two coordinates, the X-ray diagnosis apparatus 100 sets a rectangular region having a diagonal line connecting the two coordinates as a region of interest (ROI). The X-ray diagnosis apparatus 100 then generates an enlarged image of the region of interest (ROI) through the predetermined image processing and displays the enlarged image.

As such, the X-ray diagnosis apparatus 100 according to the seventh modification of the embodiments can set an ROI at a position that the user UR, such as a physician treating the subject P, intends to set, and allow the user UR to perform voice-controlled image processing to the ROI. Thus, the X-ray diagnosis apparatus 100 of the seventh modification can allow the user UR or the physician to easily apply image processing to his or her intended region even while his or her hands are being occupied with something else. Owing to such features, the X-ray diagnosis apparatus 100 of the seventh modification can improve the user UR's operability of the X-ray diagnosis apparatus 100, thereby improving the examination throughput relative to the subject P.

Eighth Modification

An eighth modification involves performing predetermined image processing different from the enlargement process to the ROI on the X-ray image XI according to the user UR's utterance. For the sake of specificity, the X-ray image XI is defined to have undergone image processing for enhancing viewability of an organ of the subject P (hereinafter, first image processing). Thus, the user UR or a radiological technician is assumed to set various kinds of parameters (hereinafter, first parameters) for the first image processing in advance depending on an organ to be imaged, prior to an examination of the subject P with the X-ray diagnosis apparatus 100.

In the eighth modification, the image processing to be applied to the ROI is defined as enhancement of a region representing a device on the X-ray image XI (hereinafter, second image processing). Examples of the device include a catheter, a guide wire, and a stent. It is assumed that various kinds of parameters for use in the second image processing (hereinafter, second parameters) are preset depending on a device type, prior to an examination of the subject P with the X-ray diagnosis apparatus 100.

The second image processing is not limited to the enhancement (change of brightness) of a device region (hereinafter, brightness changing process) and may be any kind of image processing such as noise reduction, low-frequency enhancement, profile enhancement, and high-frequency enhancement as long as the image processing uses second parameters different from the first parameters. Computer programs for executing the first image processing and the second image processing, the first parameters, and the second parameters are stored in the memory 143.

The microphone 150 collects the user UR's utterance that the second image processing is to be performed to the ROI.

The utterance denoting execution of the second image processing is different from the one in the seventh modification and may be, for example, "brightness, voice control" that denotes brightness changing control of the ROI through the second image processing. In addition to "brightness, voice control", the activation words for the voice-controlled image processing may be any other words such as "brightness control, enlarge" as long as the words represent the intention to vocally control image processing. Other words may be, for example, a term associated with words used in a physician's instruction for a technician to designate an ROI or control the second image processing.

The processing circuitry 145 then uses the speech recognition function 151 to recognize that the voice-controlled second image processing is to be performed from a user's utterance. In the eighth modification, after uttering "brightness, voice control", the user UR utters numerical values indicating the coordinate of the center of the ROI to be enlarged on the X-ray image XI or numerical values indicating two coordinates representing two endpoints of a diagonal line of an ROI if the ROI is rectangular. Collection of the processing region words and vocal ROI setting are similar to those in the seventh modification, therefore, a description thereof is omitted.

The system control unit 11 uses the image processing function 113 to change the image processing parameters to be applied to the region of interest set by the setting function 111 to parameters different from image processing parameters to be applied to the region outside the region of interest on the X-ray image, to perform predetermined image processing. Specifically, the image processing function 113 changes image processing parameters for the region of interest from the first parameters to the second parameters to perform image processing. As a result, the region of interest undergoes the second image processing. Multiple sets of second parameters may be set according to a type of the second image processing. In this case the second parameters to be applied to the ROI are selected from the second parameter sets according to a user UR's instruction given via the input interface 141, prior to an examination of the subject P.

The following will describe the steps of the voice-controlled image processing according to the eighth modification, referring to the flowchart in FIG. 13. Prior to execution of the voice-controlled image processing of FIG. 13, the first parameters for the first image processing and the second parameters for the second image processing are preset according to a user UR's instruction given via the input interface 141. The first parameters and the second parameters are stored in the memory 143.

Voice-Controlled Image Processing

Step S131

The imaging apparatus 110 generates an X-ray image of the subject P before image processing (hereinafter, unprocessed image) by irradiating the subject P with X-rays. The system control unit 11 uses the image processing function 113 to perform the first image processing to the unprocessed image using the first parameters, to generate an X-ray image XI having undergone the image processing. The display unit 10 displays the X-ray image XI.

Step S132

The microphone 150 collects activation words, e.g., "brightness, voice control", when uttered by the user UR (Yes at step S132). The microphone 150 converts the utterance into electric signals for output to the remote operator station 130. The process then proceeds to step S133. Without the user UR's utterance of the activation words (No step S132), the process proceeds to step S140.

Step S133

The processing circuitry 145 uses the speech recognition function 151 to recognize the activation words. Thereby, the speech recognition function 151 specifies the type of image processing in the voice-controlled image processing. According to the eighth modification, the speech recognition function 151 specifies the type of image processing (brightness changing process in this modification) with respect to the ROI from the recognized activation words. In response to the recognized activation words, the system control unit 11 displays the X-ray image XI with multiple numerical values NV indicating the positions on the X-ray image XI on the display unit 10. The display unit 10 may additionally display multiple scales corresponding to the numerical values NV.

The operations at step S134 and step S135 are similar to those in the seventh modification, therefore, a description thereof is omitted.

Step S136

The system control unit 11 uses the image processing function 113 to perform the second image processing to the ROI. Specifically, the image processing function 113 changes the first parameters to the second parameters to perform the second image processing to the ROI. In this manner the image processing function 113 generates an X-ray image (hereinafter, processed X-ray image) by subjecting the ROI and the region outside the ROI to different kinds of image processing.

Step S137

The system control unit 11 displays the processed X-ray image (in this modification an X-ray image containing the ROI and the region outside the ROI having undergone different kinds of image processing) on the display unit 10.

The operations at steps S138, S139, and S140 are similar to those at steps S308, S309, and S310 of FIG. 3, respectively, therefore, a description thereof is omitted.

According to the eighth modification of the embodiments as described above, the X-ray diagnosis apparatus 100 sets a predetermined region centered around a single coordinate as a region of interest when the numerical values recognized by the speech recognition function 151 indicate a single coordinate. When the recognized numerical values indicate two coordinates, the X-ray diagnosis apparatus 100 sets a rectangular region having a diagonal line connecting the two coordinates as a region of interest. The X-ray diagnosis apparatus 100 then changes the image processing parameters to be applied to the region of interest to image processing (first image processing) parameters (different from the first parameters, i.e., second parameters) for the region outside the region of interest, to perform predetermined image processing (second image processing).

As such, the X-ray diagnosis apparatus 100 of the eighth modification can allow the user UR to vocally designate the ROI and change the first image processing to the second image processing to apply the second image processing to only the designated ROI. For example, the X-ray diagnosis apparatus 100 of the eighth modification can perform image processing to the region outside the ROI using general image processing parameters (first parameters) that enable observation of an organ, and perform image processing to inside the ROI using image processing parameters (second parameters) that enable enhancement of a device, to be able to display X-ray images having undergone the image processing. The rest of the effects are the same as or similar to those of the seventh modification, therefore, a description thereof is omitted.

First Application

A first application involves integration of the seventh modification and the eighth modification. Thus, the activation words in the first application may be, for example, "voice-controlled image processing". Also, in the first application, the words to be uttered after the activation words, i.e., at step S134, include an intention for enlargement or a change of brightness in addition to the numerical values indicating the coordinate of the center of the ROI to be enlarged on the X-ray image XI or the numerical values indicating two coordinates of two endpoints of a diagonal line of an ROI if the ROI is rectangular. The effects of the first application are the same as or similar to those of the seventh modification and the eighth modification, therefore, a description thereof is omitted.

Second Application

A second application involves suitably combining the embodiments, the first to eighth modifications, and the first application. Thereby, the second application enables control of the diaphragm blades, the couch 5, or the image processing according to a user UR's intention. In the second application, in response to the utterance of the activation words at step S132, the same operations in the embodiments and the first to eighth modifications are performed. The effects of the second application are the same as or similar to those of the embodiments, the seventh modification, the eighth modification, and the first application, therefore, a description thereof is omitted.

To implement the technical idea of one embodiment by an X-ray imaging control method, the X-ray imaging control method includes generating an X-ray image XI by X-ray imaging of the subject P by the imaging system 110 which includes the X-ray tube 1*a* that generates an X-ray, the X-ray diaphragm 1*b* that restricts an irradiation range of the X-ray, the X-ray detector unit 3 that detects the X-ray, and the couch 5 on which the subject P is to be laid for irradiation with the X-ray; displaying the X-ray image XI with a plurality of numerical values indicating positions on the X-ray image XI; recognizing a numerical value from a collected user UR's utterance with respect to the plurality of numerical values; and performing control of the imaging system 110 in accordance with a position indicated by the recognized numerical value among the plurality of numerical values. The procedure of the X-ray imaging control method corresponds to that of the voice moving-control process or the voice-controlled image processing, therefore, a description thereof is omitted. The effects of the X-ray imaging control method are the same as or similar to those of the embodiments, the seventh modification, the eighth modification, the first application, and the second application, therefore, a description thereof is omitted.

Third Application

A third application involves displaying the user UR's utterance and/or the numerical value recognized by the speech recognition function 151 on the display unit 10. In the third application the display unit 10 displays characters and/or numbers included in the moving instruction words MIW. This operation is performed at, for example, step S305 of FIG. 3 in the third application.

The processing circuitry 145 uses the speech recognition function 151 to perform speech recognition of electric signals representing the user UR's utterance collected by the microphone 150. The speech recognition function 151 stores a result of the recognition of the user UR's utterance in the memory 143. The recognition result includes, for example, the user UR's utterance and/or the numerical value recognized by the speech recognition function 151.

The system control unit 11 displays the recognition result of the user UR's utterance on the display unit 10. The display unit 10 thus displays the user UR's utterance and/or the numerical value as recognized. The display unit 10 may display the user UR's utterance and/or the numerical value in order that the speech recognition function 151 recognized. That is, the display unit 10 may display the recognition result of the user UR's utterance in real time and in sequence in the order of utterance of the moving instruction words MIW.

Figure 14:
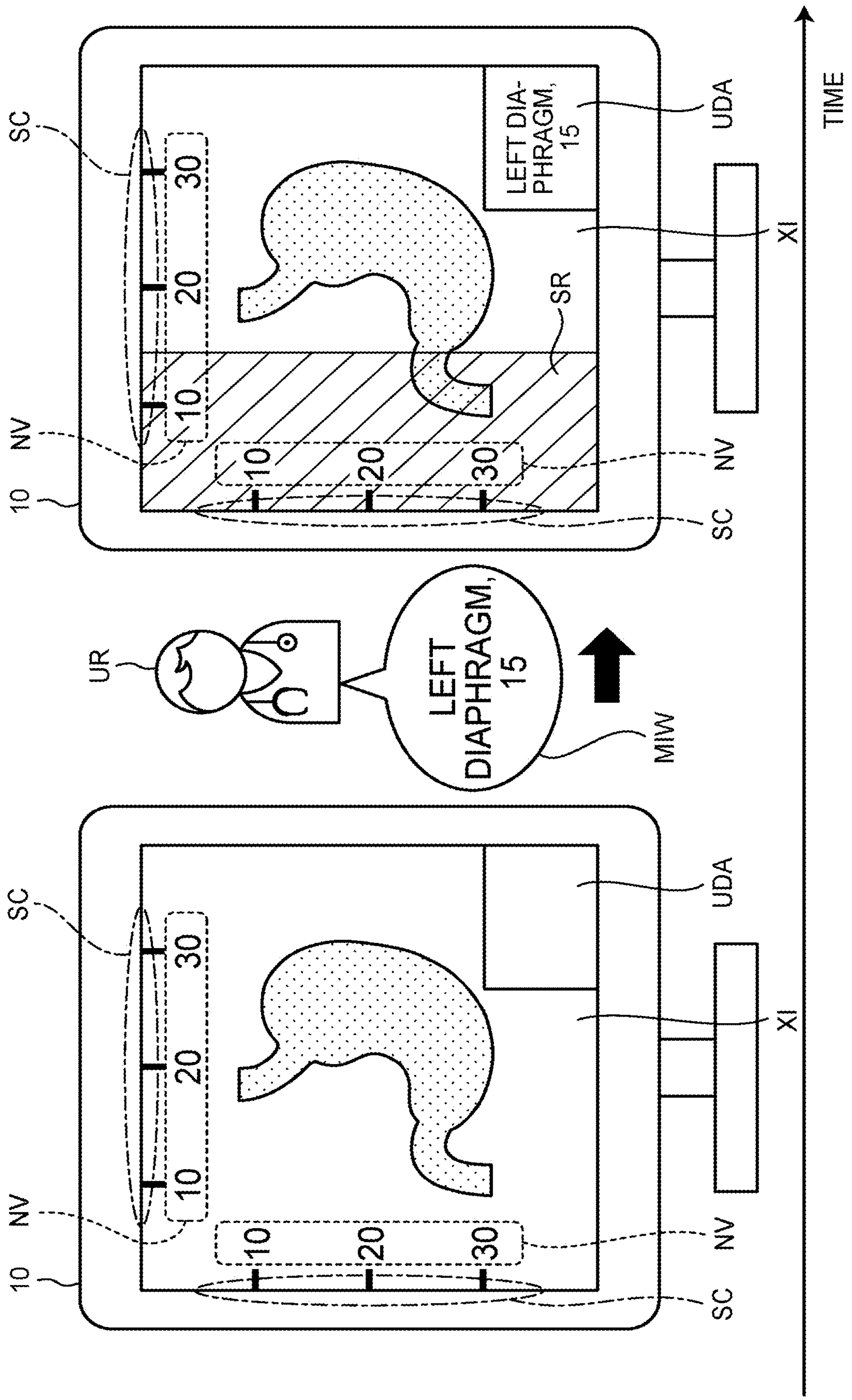
FIG. 14 illustrates one example of a display before and after the user has spoken moving instruction words "left diaphragm, 15" according to a third application of some embodiments.

FIG. 14 depicts an example of a display before and after the user UR utters the moving instruction words MIW "left diaphragm, 15". As illustrated in FIG. 14, before the utterance of the moving instruction words MIW, a display area (hereinafter, utterance display area) UDA for displaying the recognition result of the user UR's utterance, i.e., moving instruction words MIW, displays none. As illustrated in FIG. 14, in response to the utterance of the moving instruction words MIW, the display unit 10 displays the moving instruction words "left diaphragm, 15" on the utterance display area UDA as the recognition result of the user UR's utterance. In other words, in the example of FIG. 14, the display unit 10 displays the recognized user UR's words "left diaphragm" and the recognized numerical value "15" on the utterance display area UDA.

According to the third application of the embodiments as described above, the X-ray diagnosis apparatus 100 recognizes the user UR's utterance and displays the user UR's words and and/or the numerical value as recognized. As a result, the X-ray diagnosis apparatus 100 of the third application of the embodiments can display the user UR's diaphragm control instruction (recognition result) recognized by the speech recognition function 151 by characters on the display unit 10, as illustrated in FIG. 14. This makes it possible for the user UR to confirm that the speech recognition function 151 has correctly recognized his or her utterance. In other words, the X-ray diagnosis apparatus 100 of the third application of the embodiments can facilitate the communications between the user UR and the X-ray diagnosis apparatus 100. The rest of the effects are the same as or similar to that in the embodiments, therefore, a description thereof is omitted.

Fourth Application

A fourth application involves displaying the numerical value recognized by the speech recognition function 151 on the display unit 10. This operation is performed at, for example, step S305 of FIG. 3 in the fourth application.

The system control unit 11 displays the recognized numerical value in a highlighted manner on the scales SC corresponding to the numerical values NV. Examples of intensified display of the recognized numerical value include highlighting or blinking of the recognized numerical value, or placing a distinct symbol in the position of the recognized numerical value. Examples of the symbol include various kinds of graphics such as a circle or star symbol surrounding the recognized numerical value and a sparkle or halo applied to the recognized numerical value.

In the following, the display unit 10 is defined to display the numerical value recognized by the speech recognition function 151 on the scales SC in a highlighted manner, for the sake of simpler explanation. Specifically, when the numerical value recognized by the speech recognition function 151 does not match any of the scales SC, the system control unit 11 displays the recognized numerical value in a highlighted manner on the display unit 10.

Figure 15:
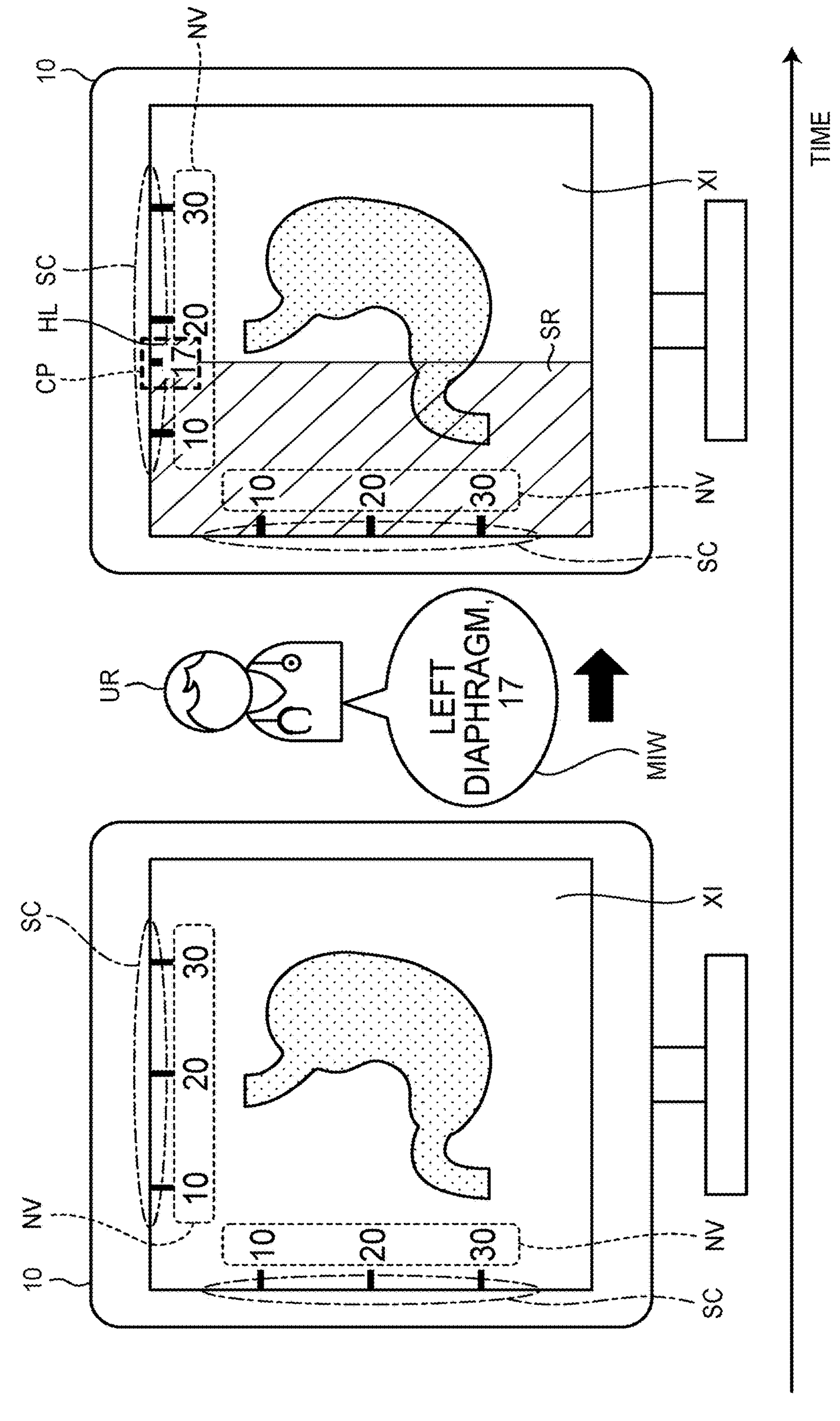
FIG. 15 illustrates one example of a display showing a numerical value recognized by a speech recognition function in a highlighted manner according to a fourth application of some embodiments.

FIG. 15 depicts an example of a display of the numerical value recognized by the speech recognition function 151 by highlighting HL. FIG. 15 depicts a display before and after the user UR utters the moving instruction words MIW “left diaphragm, 17”, as an example. As illustrated in FIG. 15, in response to the utterance of the moving instruction words MIW, the display unit 10 displays the numerical value of 17 included in the moving instruction words MIW “left diaphragm, 17” on the scales SC by highlighting HL.

According to the fourth application of the embodiments as described above, the X-ray diagnosis apparatus 100 displays the recognized numerical value in a highlighted manner on the scales SC corresponding to the numerical values NV. As a result, the X-ray diagnosis apparatus 100 of the fourth application of the embodiments can allow the user UR to know the numerical value indicating the current diaphragm position at a glance. The rest of the effects of the fourth application are the same or similar to those of the embodiments and the third application, therefore, a description thereof is omitted.

According to at least one of the embodiments, modifications, and applications, it is made possible for the user to properly control the X-ray diagnosis apparatus 100 in accordance with his or her intentions.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

With respect to the embodiments, modifications, and applications as above, the following subjoinders describing an aspect and selective features of the inventions will be presented.

Subjoinder 1:

An X-ray diagnosis apparatus includes an imaging system including an X-ray tube that generates an X-ray, an X-ray diaphragm that restricts an irradiation range of the X-ray, an X-ray detector unit that detects the X-ray, and a couch on which a subject is to be laid for irradiation with the X-ray; a display unit that displays an X-ray image with a plurality of numerical values indicating positions on the X-ray image generated by X-ray imaging of the subject by the imaging system; a speech recognition unit configured to recognize a numerical value based on a collected user’s utterance with respect to the plurality of numerical values; and a control unit configured to perform control of the imaging system in accordance with a position indicated by the recognized numerical value among the plurality of numerical values.

Subjoinder 2:

The X-ray diaphragm may include a plurality of diaphragm blades. The control unit may control the X-ray diaphragm to move at least one of the plurality of diaphragm blades to the position indicated by the recognized numerical value.

Subjoinder 3:

The plurality of diaphragm blades of the X-ray diaphragm may include two opposing diaphragm blades. The speech recognition unit may recognize one of the two opposing diaphragm blades from the user’s utterance. The control unit may control the X-ray diaphragm to move the one diaphragm blade to the position indicated by the recognized numerical value.

Subjoinder 4:

The plurality of diaphragm blades of the X-ray diaphragm may include two opposing diaphragm blades. The speech recognition unit may recognize the two opposing diaphragm blades from the user’s utterance. The control unit may control the X-ray diaphragm to move the two opposing diaphragm blades to the position indicated by the recognized numerical value in a symmetrical manner.

Subjoinder 5:

The speech recognition unit may recognize a numerical value indicating a center of the irradiation range of the X-ray from the user’s utterance. The control unit may control the X-ray diaphragm to independently move the plurality of diaphragm blades such that the position indicated by the recognized numerical value matches the center of the irradiation range.

Subjoinder 6:

The X-ray diaphragm may include a plurality of diaphragm blades. The display unit may additionally display a plurality of scales corresponding to the plurality of numerical values, and a numerical value and a scale indicating a current position of one of the plurality of diaphragm blades.

Subjoinder 7:

The user’s utterance may contain a relative value to a current position of one of the plurality of diaphragm blades.

Subjoinder 8:

The control unit may control the couch to be moved to the position indicated by the recognized numerical value.

Subjoinder 9:

The speech recognition unit may recognize a numerical value to match a center of the irradiation range of the X-ray from the user’s utterance. The control unit may control the couch such that the recognized numerical value matches the center of the irradiation range.

Subjoinder 10:

The user’s utterance may contain a relative value to a current position of the couch.

Subjoinder 11:

The X-ray diagnosis apparatus may further include a setting unit configured to set a region of interest on the X-ray image based on the recognized numerical value, and an image processing unit configured to perform predetermined image processing to the region of interest. The display unit may display the X-ray image having undergone the predetermined image processing.

Subjoinder 12:

When the recognized numerical value corresponds to one coordinate, the setting unit may set a predetermined region centered around the one coordinate as the region of interest. When the recognized numerical value corresponds to two coordinates, the setting unit may set a rectangular region having a diagonal line connecting the two coordinates as the region of interest. The setting unit may then generate an enlarged image of the region of interest through the predetermined image processing. The display unit may display the enlarged image.

Subjoinder 13:

When the recognized numerical value corresponds to one coordinate, the setting unit may set a predetermined region centered around the one coordinate as the region of interest. When the recognized numerical value corresponds to two coordinates, the setting unit may set a rectangular region having a diagonal line connecting the two coordinates as the region of interest. The image processing unit may change an image processing parameter to be applied to the region of interest to a parameter different from an image processing parameter for a region outside the region of interest, to perform the predetermined image processing.

Subjoinder 14:

The control unit may hide the plurality of numerical values on the display unit when a predetermined time has passed from the display of the plurality of numerical values on the display unit.

Subjoinder 15:

The display unit may additionally display a plurality of scales corresponding to the plurality of numerical values. The speech recognition unit may recognize a numerical value not matching any of the plurality of scales from the user's utterance.

Subjoinder 16:

The display unit may additionally display a plurality of scales corresponding to the plurality of numerical values, and a plurality of guidelines corresponding to the plurality of scales.

Subjoinder 17:

The display unit may display the plurality of numerical values outside the X-ray image.

Subjoinder 18:

The speech recognition unit may recognize the user's utterance. The display unit may display the recognized user's utterance and/or the recognized numerical value.

Subjoinder 19:

The display unit may display the recognized numerical value in a highlighted manner on the plurality of scales corresponding to the plurality of numerical values.

Subjoinder 20:

An X-ray imaging control method includes generating an X-ray image by X-ray imaging of a subject by an imaging system, the imaging system including an X-ray tube that generates an X-ray, an X-ray diaphragm that restricts an irradiation range of the X-ray, an X-ray detector unit that detects the X-ray, and a couch on which a subject is to be laid for irradiation with the X-ray; displaying the X-ray image with a plurality of numerical values indicating positions on the X-ray image; recognizing a numerical value based on a collected user's utterance with respect to the plurality of numerical values; and performing control of the imaging system in accordance with a position indicated by the recognized numerical value among the plurality of numerical values.

What is claimed is:

1. An X-ray diagnosis apparatus comprising:
- an imaging system comprising
  - an X-ray tube that generates an X-ray,
  - an X-ray diaphragm that restricts an irradiation range of the X-ray,
  - an X-ray detector that detects the X-ray, and
  - a couch on which a subject is to be laid for irradiation with the X-ray;
- a display that displays an X-ray image with a plurality of numerical values indicating positions on the X-ray image generated by X-ray imaging of the subject by the imaging system;
- display control circuitry configured to cause the display to display the X-ray image with the plurality of numerical values indicating positions on the X-ray image generated by X-ray imaging of the subject by the imaging system;
- processing circuitry configured to recognize a numerical value related to the plurality of numerical values based on a collected user's utterance with respect to the plurality of numerical values; and
- system control circuitry configured to perform control of the imaging system in accordance with a position indicated by the recognized numerical value among the plurality of numerical values.

2. The X-ray diagnosis apparatus according to claim 1, wherein
- the X-ray diaphragm includes a plurality of diaphragm blades, and
- the system control circuitry is further configured to control the X-ray diaphragm to move at least one of the plurality of diaphragm blades to the position indicated by the recognized numerical value.

3. The X-ray diagnosis apparatus according to claim 2, wherein
- the plurality of diaphragm blades of the X-ray diaphragm includes two opposing diaphragm blades, and
- the processing circuitry further is configured to recognize one of the two opposing diaphragm blades from the user's utterance, and
- the system control circuitry further is configured to control the X-ray diaphragm to move the one diaphragm blade to the position indicated by the recognized numerical value.

4. The X-ray diagnosis apparatus according to claim 3, wherein
- the processing circuitry is further configured to recognize a numerical value indicating a center of the irradiation range of the X-ray from the user's utterance, and
- the system control circuitry is further configured to control the X-ray diaphragm to independently move the plurality of diaphragm blades such that the position indicated by the recognized numerical value matches the center of the irradiation range.

5. The X-ray diagnosis apparatus according to claim 2, wherein
- the plurality of diaphragm blades of the X-ray diaphragm includes two opposing diaphragm blades, the processing circuitry is further configured to recognize the two opposing diaphragm blades from the user's utterance, and the system control circuitry is further configured to control the X-ray diaphragm to move the two opposing diaphragm blades to the position indicated by the recognized numerical value in a symmetrical manner.

6. The X-ray diagnosis apparatus according to claim 2, wherein the user's utterance contains a relative value to a current position of one of the plurality of diaphragm blades.

7. The X-ray diagnosis apparatus according to claim 1, wherein the X-ray diaphragm includes a plurality of diaphragm blades, and the display additionally displays a plurality of scales corresponding to the plurality of numerical values, and a numerical value and a scale indicating a current position of one of the plurality of diaphragm blades.

8. The X-ray diagnosis apparatus according to claim 1, wherein the system control circuitry is further configured to control the couch to be moved to the position indicated by the recognized numerical value.

9. The X-ray diagnosis apparatus according to claim 8, wherein the processing circuitry is further configured to recognize a numerical value to match a center of the irradiation range of the X-ray from the user's utterance, and the system control circuitry is further configured to control the couch such that the recognized numerical value matches the center of the irradiation range.

10. The X-ray diagnosis apparatus according to claim 8, wherein the user's utterance contains a relative value to a current position of the couch.

11. The X-ray diagnosis apparatus according to claim 1, wherein the system control circuitry is further configured to:

set a region of interest on the X-ray image based on the recognized numerical value, and perform predetermined image processing to the region of interest, and the display displays the X-ray image having undergone the predetermined image processing.

12. The X-ray diagnosis apparatus according to claim 11, wherein the system control circuitry is further configured to:

when the recognized numerical value corresponds to one coordinate, set a predetermined region centered around the one coordinate as the region of interest, when the recognized numerical value corresponds to two coordinates, set a rectangular region having a diagonal line connecting the two coordinates as the region of interest, and generate an enlarged image of the region of interest through the predetermined image processing, and the display displays the enlarged image.

13. The X-ray diagnosis apparatus according to claim 11, wherein the system control circuitry is further configured to:

when the recognized numerical value corresponds to one coordinate, set a predetermined region centered around the one coordinate as the region of interest, when the recognized numerical value corresponds to two coordinates, set a rectangular region having a diagonal line connecting the two coordinates as the region of interest, and change an image processing parameter to be applied to the region of interest to a parameter different from an image processing parameter for a region outside the region of interest, to perform the predetermined image processing.

14. The X-ray diagnosis apparatus according to claim 1, wherein the system control circuitry is further configured to hide the plurality of numerical values on the display when a predetermined time has passed from the display of the plurality of numerical values on the display.

15. The X-ray diagnosis apparatus according to claim 1, wherein the display additionally displays a plurality of scales corresponding to the plurality of numerical values, and the processing circuitry is further configured to recognize a numerical value not matching any of the plurality of scales from the user's utterance.

16. The X-ray diagnosis apparatus according to claim 1, wherein the display additionally displays a plurality of scales corresponding to the plurality of numerical values, and a plurality of guidelines corresponding to the plurality of scales.

17. The X-ray diagnosis apparatus according to claim 1, wherein the display displays the plurality of numerical values outside the X-ray image.

18. The X-ray diagnosis apparatus according to claim 1, wherein the processing circuitry is further configured to recognize the user's utterance, and the display displays the recognized user's utterance and/or the recognized numerical value.

19. The X-ray diagnosis apparatus according to claim 1, wherein the display displays the recognized numerical value in a highlighted manner on the plurality of scales corresponding to the plurality of numerical values.

20. An X-ray imaging control method, comprising:

generating an X-ray image by X-ray imaging of a subject by an imaging system, the imaging system comprising an X-ray tube that generates an X-ray, an X-ray diaphragm that restricts an irradiation range of the X-ray, an X-ray detector that detects the X-ray, and a couch on which the subject is to be laid for irradiation with the X-ray;

displaying the X-ray image with a plurality of numerical values indicating positions on the X-ray image generated by X-ray imaging of the subject by the imaging system;

recognizing a numerical value related to the plurality of numerical values based on a collected user's utterance with respect to the plurality of numerical values; and performing control of the imaging system in accordance with a position indicated by the recognized numerical value among the plurality of numerical values.

* * * * *